United States Patent
Lin et al.

(10) Patent No.: US 6,855,695 B2
(45) Date of Patent: Feb. 15, 2005

(54) WATER-SOLUBLE SHPS AS NOVEL ALKYLATING AGENTS

(75) Inventors: Xu Lin, Brandford, CT (US); Terrence W. Doyle, Killingworth, CT (US); Ivan King, North Haven, CT (US)

(73) Assignee: Vion Pharmaceuticals, Inc., New Haven, CT (US)

( * ) Notice: Subject to any disclaimer, the term of this patent is extended or adjusted under 35 U.S.C. 154(b) by 16 days.

(21) Appl. No.: 10/461,282

(22) Filed: Jun. 13, 2003

(65) Prior Publication Data
US 2004/0254103 A1 Dec. 16, 2004

(51) Int. Cl.$^7$ .................... A61K 38/00; A61K 38/04
(52) U.S. Cl. .................... 514/12; 514/13; 514/14; 514/15; 514/16; 514/17; 514/18; 514/19; 530/324; 530/325; 530/326; 530/327; 530/328; 530/329; 530/330
(58) Field of Search .................... 514/12, 13, 14, 514/15, 16, 17, 18, 19, 7, 115, 590, 562, 521, 534; 530/324, 325, 326, 327, 328, 329, 330, 331; 564/35; 562/824, 430; 558/190

(56) References Cited

U.S. PATENT DOCUMENTS

| | | | |
|---|---|---|---|
| 4,175,200 A | 11/1979 | Hunter et al. | 560/1 |
| 4,385,055 A | 5/1983 | Klayman et al. | 514/253.01 |
| 4,447,427 A | 5/1984 | Klayman et al. | 514/210.18 |
| 4,684,747 A | 8/1987 | Sartorelli et al. | 564/81 |
| 4,696,938 A | 9/1987 | Le | 514/343 |
| 4,849,563 A * | 7/1989 | Sartorelli et al. | 514/155 |
| 5,101,072 A | 3/1992 | Sartorelli et al. | 564/81 |
| 5,214,068 A | 5/1993 | Sartorelli et al. | 514/601 |
| 5,256,820 A | 10/1993 | Sartorelli et al. | 564/81 |
| 5,637,619 A * | 6/1997 | Sartorelli et al. | 514/590 |
| 5,767,134 A | 6/1998 | Li et al. | 514/353 |
| 6,696,487 B2 * | 2/2004 | Gerusz et al. | 514/256 |

FOREIGN PATENT DOCUMENTS

WO — WO 02/30424 A1 — 4/2002

OTHER PUBLICATIONS

Burchenal et al, Cancer The Outlaw Cell, Richard E. Lafond, editor,American Chemical Society , 1988 pp. 204–205.*
Gura, Science, vol. 278 Nov. 7, 1997, pp. 1041–1042.*
Shyam et al. "Synthesis and Evaluation of N,N'–Bis(arylsulfonyl)hydrazines . . . " J. Med. Chem. 28, 525 (1985).
Hrubiec et al. "Synthesis and Evaluation . . . " J. Med. Chem 29, 1777 (1986).
Shyam et al. "1,2–Bis (arylsufonyl) hydrazines 2." J. Med. Chem. 29, 1323 (1986).
Hrubiec et al. "Synthesis and Evaluation . . . " J. Med. Chem. 29, 1299 (1986).
Shyam et al. "1,2–Bis(sulfonyl)hydrazines 3" J. Med. Chem. 30, 2157 (1987).
Shyam et al. "Synthesis and Evaluation . . . " J. Med. Chem. 33, 2259 (1990).
Shyam et al., "Synthesis and Evaluation . . . " J. Med. Chem. 36, 3496 (1993).
Penketh et al. "Studies on the Mechanism . . . " J. Med. Chem. 37, 2912 (1994).
Burchenal et al., Cancer: The Outlaw Cell, Richard E. Lafond, editor American Chemical Society, 1988, pp. 204–205.
Gura, Science, vol. 278, Nov. 7, 1997, pp. 1041–1042.

* cited by examiner

*Primary Examiner*—Christopher R. Tate
*Assistant Examiner*—Edward Ward
(74) *Attorney, Agent, or Firm*—Henry D. Coleman; R. Neil Sudol; William J. Sapone

(57) ABSTRACT

The present invention relates to compounds according to the structure (I):

$$\text{MeO}_2\text{S}-\text{N}(\text{R})-\text{N}(\text{SO}_2\text{Me})-\text{C}(=\text{O})-\text{N}(\text{R}')-\text{CH}_2-\text{Ar}(R_2,R_3,R_4,R_5,R_6)$$

Where R is —CH$_3$ or —CH$_2$CH$_2$Cl; R' is C$_1$–C$_7$ alkyl or —CH$_2$CH$_2$Cl; R$_2$ or R$_4$ is OPO$_3$H$_2$, NO$_2$, OCO(Glu-OH), NHCO(Glu-OH), NHR$_7$ and unassigned groups of R$_2$, R$_3$, R$_4$, R$_5$ and R$_6$ are, independently H, F, Cl, Br, I, OH, OPO$_3$H$_2$, OCH$_3$, CF$_3$, OCF$_3$, NO$_2$, CN, SO$_2$CH$_3$, SO$_2$CF$_3$, COCH$_3$, COOCH$_3$, SCH$_3$, SF$_5$, NH$_2$, NHR$_7$, N(CH$_3$)$_2$, OPO$_3$H$_2$, or a C1–C7 alkyl group with the proviso that when any two of unassigned groups of R$_2$, R$_3$, R$_4$, R$_5$ or R$_6$ are other than H, the other two of unassigned groups of R$_2$, R$_3$, R$_4$, R$_5$ or R$_6$ are H. R$_7$ is H or polyglutamyl as described. Phosphoric acid and glutamic acid can be a free acid or pharmaceutically acceptable salt thereof.

73 Claims, 15 Drawing Sheets

Efficacy of 19-22 on B16-F10 Murine Melanoma in Mice

Survival Rate of Tumor-bearing Mice Receiving 19-22

Toxicity of 19-22 on B16F10 Melanoma in C57BL/6 Mice

Efficacy of 19-22 on HTB177 Melanoma on Nu/nu CD1 Mice

Toxicity of 19-22 on HTB177 Melanoma in Nu/nu CD1 Mice

WATER-SOLUBLE SHPS AS NOVEL ALKYLATING AGENTS

This invention was made with government support under grant number 1 R43 CA92968-01 awarded by the Department of Health and Human Services. As such, the government retains certain rights in the invention.

FIELD OF THE INVENTION

The present invention relates to metabolically activated sulfonyl hydrazine prodrugs (SHPs) exhibiting anti-tumor activity in mammals. Methods of treating neoplasia, especially including cancer, using compounds according to the present invention, are additional aspects of the present invention.

BACKGROUND OF THE INVENTION

Alkylating agents are among the most effective therapeutic agents currently available to treat different malignancies, and are widely used in the clinic (Katzung, In *Basic& Clinical Pharmacology*, 7th edition, 1998, Appleton & Lange, Stamford, 881). The high degree of cytotoxicity is attributed to the ability to induce DNA interstrand cross-linking thereby inhibiting replication (Rajski and Williams, *Chem Reviews* 1998, 98: 2723). Among the alkylating agents, the CNU (chloroethylnitrosourea) series have been widely used clinically to treat brain tumors, colon cancer and lymphomas (DeVita, et al. *Cancer Res.* 1965, 25; 1876; and Nissen, et al. *Cancer* 1979, 43: 31), however, their clinical usefulness is limited due to delayed and cumulative bone marrow depression and hepatic toxicity (Panasci, et al. *Cancer Res.* 1977, 37: 2615; and Gibson and Hickman, *Biochem Pharmacol.* 1982, 31: 2795).

A series of 1,2-bis(sulfonyl)hydrazine prodrugs (SHPs) with the ability to generate chloroethylating and carbamoylating species, but lacking hydroxyethylating and vinylating species, generated by the CNUs had been developed recently (Sartorelli, et al. see U.S. Pat. No. 6,040,338; U.S. Pat. No. 5,637,619; U.S. Pat. No. 5,256,820; U.S. Pat. No. 5,214,068; U.S. Pat. No. 5,101,072; U.S. Pat. No. 4,849,563; and U.S. Pat. No. 4,684,747. The antitumor activity has been suggested to result from chloroethylating and subsequent cross-linking of DNA (Kohn, In *Recent Results in Cancer Research*, Eds. Carter, et al., 1981, Springer, Berlin, vol. 76: 141; and Shealy, et al., *J Med Chem.* 1984, 27: 664). The carbamoylating species (i.e., the isocyanate) can react with thiol and amine functionalities on proteins and inhibit DNA polymerase (Baril, et al. *Cancer Res.* 1975, 35: 1), the repair of DNA strand breaks (Kann, et al. *Cancer Res.* 1974, 34: 398) and RNA synthesis and processing (Kann, et al. *Cancer Res.* 1974, 34: 1982). However, hydroxyethylation of DNA is a carcinogenic and/or mutagenic event (Swenson, et al. *J Natl Cancer Inst.* 1979, 63: 1469).

1,2-Bis(methylsulfonyl)-1-(2-chloroethyl)-2-(methylaminocarbonyl) hydrazine (VNP40101M), the current lead compound in the SHP series, has lower toxicity to hosts and better anti-tumor activities against the L1210 murine leukemia, L1210/BCNU, L1210/CTX, L1210/MEL (1,3-bis(2-chloroethyl)-1-nitrosourea, cyclophosphamide and melphalan resistant sublines), P388 leukemia, M109 lung carcinoma, B16 melanoma, C26 colon carcinoma and U251 glioma than chloroethylnitrosourea (CNU) derivatives and other SHP analogs (Shyam, et al. *J Med Chem.* 1999, 42: 941). In addition, VNP40101 M is effective in crossing the blood brain barrier (BBB) and eradicating leukemia cells implanted intracranially (>6.54 log cell kill), rivaling the efficacy of BCNU (Finch, et al. *Cancer Biochem Biophys.* 2001, 61: 3033).

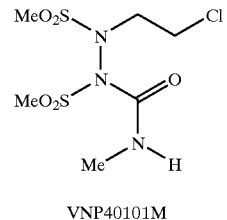

VNP40101M

The anti-tumor activity of VNP40101M is probably due to the release of 90CE and methyl isocyanate. 90CE further fragments to yield methyl 2-chloroethyldiazosulfone (1) FIG. 1, a relatively specific $O^6$-guanine chloroethylator, producing minimal alkylation of the $N^7$-position of guanine (Penketh, et al. *J Med Chem.* 1994, 37: 2912; and Penketh, et al. *Biochem Pharmacol.* 2000, 59: 283). Methyl isocyanate released from VNP40101M has the ability to inhibit various DNA repair enzymes including $O^6$-alkylguanine-DNA alkyltransferase leading to stabilization of the $O^6$-alkylguanine monoalkyl species in DNA, which leads to a larger percentage of interstrand cross-links (Baril, et al. *Cancer Res.* 1975, 35: 1).

VNP40101M is currently in clinical trials in patients with solid tumors and hematologic malignancies. VNP40101M is not very soluble in aqueous solution; polyethylene glycol (PEG) and ethanol are included in the vehicle of the finished product to promote solubility. Both PEG and ethanol are acceptable vehicles for human use but may cause side effects such as hemolysis and phlebitis at high concentrations, as indicated in animal studies. VNP40101M is very well tolerated in humans and could be given at higher doses, and could in theory produce a higher degree of efficacy, if PEG and ethanol could be eliminated from the vehicle. Therefore, our aim was to synthesize a series of SHPs that (a) were capable of improving its water-solubility and stability in aqueous solution at pH 3 to 9; (b) were capable of forming chloroethylating species; (c) were devoid of hydroxyethylating activity; (d) were capable of forming methyl isocyanate; and (e) were capable of improving pharmacokinetic profiles (e.g., longer half-life in vivo).

The present inventors conceived that water-soluble enzymatically-activated SHPs (I) might satisfy the above conditions. An example of such an SHP would be the phosphate containing derivatives shown in FIG. 2 for the following reasons:

(a) In general, a phosphate-bearing analog, including its salt form may have good water-solubility and stability at neutral pH;

(b) The bioconversion of compounds of general structure I is believed to proceed via alkaline phosphatase (AP) cleavage of the oxygen-phosphorous bond to form the phenol intermediate, which may subsequently undergo fragmentation resulting in the formation of chloroethylating or methylating species and carbamoylating agent without generating hydroxyethylating agent, as shown in FIGS. 1 and 2.

(c) The bioconversion of compounds I may also generate a quinone methide which itself can cause damage to DNA and thereby contribute to inhibition of cellular replication (Lin, et al. *J Med Chem.* 1986, 29: 84).

(d) Compounds I may be considered as prodrugs of VNP40101M that has been identified as an alkylating agent against a broad anticancer spectrum of neoplastic disease states, including, for example, numerous solid tumors. Thus, compounds I may generate the same active species as VNP40101M.

Further examples of bioactivated prodrugs are shown in FIGS. 3 and 4. The nitro analogs shown in FIG. 3 are examples of compounds that would be both water soluble and selectively activated under conditions of hypoxia. Release of VNP400101M would only occur on reduction of the nitro group under conditions of hypoxia. Compounds II would be reduced by nitroreductase (NR) to the corresponding amino analogs, which would be subsequently fragmented into VNP40101M and a quinone-imine methide. NR, an enzyme isolated from *E. Coli* or *Bacillus* spp., is widely used in ADEPT (antibody-directed enzyme prodrug therapy) or GDEPT (gene-directed enzyme prodrug therapy) for cancer therapy (Anlezark, et al. WO93/08288, 1993).

FIG. 4 illustrates the use of peptidases to generate VNP40101 M intratumorally. Cleavage of compounds derived from conjugation of glutamyl residues to appropriately substituted phenols and aromatic amines by carboxypeptidases such as carboxypeptidase G2 (CPG2) and carboxypeptidase A (CPA) has been shown previously. CPG2, an enzyme isolated from *Pseudomonas*, is capable of removing glutamate residues from folates and methotrexate. It has been employed in the ADEPT or GDEPT system to activate prodrugs containing glutamate residues (Bagshawe, et al. WO88/07378, 1988; Springer, et al. U.S. Pat. No. 6,025,340, 2000; Springer, et al. U.S. Pat. No. 6,004,550, 1999). CPA from bovine pancreas readily cleaves drug α-peptides (derivatives in which an amino acid is linked to the α-carboxyl group of the glutamate moiety). Also, it has been employed in the ADEPT (Wolfe, et al. *Bioconjug Chem.* 1999, 10: 38; Huennekens, *Adv Enzyme Regul.* 1997, 37: 77; and Vitols, et al. *Cancer Res.* 1995, 55: 478). As shown in FIG. 4, Compounds III and Compounds IV would be cleaved by the corresponding CPG2 or CPA, which may either be introduced as an antibody conjugate or a transgene (Pawelek, et al. U.S. Pat. No. 6,190,657, 2001), to form VNP40101M and a quinone methide or quinone-imine methide.

OBJECTS OF THE INVENTION

In one aspect, an object of the present invention is to provide compounds, pharmaceutical compositions and methods for the treatments of neoplasia, including animal and human cancer.

In another aspect of the invention, an object of the present invention is to provide methods of treating neoplasia utilizing compositions that exhibit favorable and enhanced characteristics of activity, pharmacokinetics, bioavailability and reduced toxicity.

It is yet another object of the invention to provide compositions and methods for the treatment of cancers which are resistant to treatment with traditional chemotherapeutic agents.

One or more of these and/or other objects of the invention may be readily gleaned from the description of the invention that follows.

BRIEF DESCRIPTION OF THE INVENTION

The present invention relates to compounds or their pharmaceutically acceptable salts according to the structure (I):

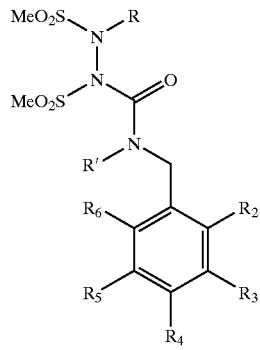

Where
R is —$CH_3$ or —$CH_2CH_2Cl$;
R' is $C_1$–$C_7$ alkyl or —$CH_2CH_2Cl$; one of $R_2$ or $R_4$, but not both, is selected from $OPO_3Hz$, $NO_2$, OCO(Glu), NHCO(Glu) and $NHR_7$ and the other of $R_2$ or $R_4$ which is unassigned, and $R_3$, $R_5$ and $R_6$, are, independently selected from H, F, Cl, Br, I, OH, $OPO_3H_2$, $OCH_3$, $CF_3$, $OCF_3$, $NO_2$, CN, $SO_2CH_3$, $SO_2CF_3$, $COCH_3$, $COOCH_3$, $SCH_3$, $SF_5$, $NHR_5$, $N(R_9)_2$, $OPO_3H_2$ and C—$C_7$ alkyl, with the proviso that at least two of $R_2$, $R_3$, $R_4$, $R_5$ and $R_6$ are H;
$R_7$ is H, glutamyl, preferably α-glutamyl (—COCH($NH_2$)$CH_2CH_2CO_2H$) or a polyglutamic acid polypeptide residue (—COCH($NHR_{7a}$)$CH_2CH_2CO_2H$ where $R_{7a}$ is glutamyl (preferably, α-glutamyl) or a polyglutamic acid polypeptide residue) having from 1 to 50 peptide linkages, preferably from 2 to 10 peptide linkages;
$R_8$ is H or $C_1$–$C_7$ alkyl; and
$R_9$ is $CH_3$ or $CH_2CH_3$. The phosphoric acid and/or glutamic acid substituents can be in the free acid form or a pharmaceutically acceptable salt thereof.

In certain preferred aspects of the present invention, preferred agents in the class of Compounds I are ortho-phosphate-bearing series where R is —$CH_2CH_2Cl$; R' is —$CH_3$; $R_2$ is a phosphate group which can be the free acid or its pharmaceutically acceptable salt (preferably Na). In particularly preferred aspects of the ortho-phosphate-bearing SHPs, $R_4$ is Cl, F or Br (preferably Cl) when $R_3$, $R_5$ and $R_6$ are H. In other preferred aspects of the ortho-phosphate-bearing SHPs, $R_5$ is Cl, F or Br (preferably Cl, F) when $R_3$, $R_4$ and $R_6$ are H. Still in other preferred aspects of the ortho-phosphate-bearing SHPs, two of $R_3$, $R_4$, $R_5$ and $R_6$ are selected from F, Cl, Br or I (preferably, both substituents are the same and more preferably, both substituents are Cl), the other two of $R_3$, $R_4$, $R_5$ and $R_6$ are H.

Preferred agents in the class of Compounds II are meta-phosphate-bearing nitro-containing analogs of SHPs. The phosphate group can be the free acid or its pharmaceutically acceptable salt (preferably Na). In a particularly preferred aspects of the nitro-containing SHPs, $R_2$ is $NO_2$ when $R_4$ is H. In other preferred aspects of the nitro-containing SHPs, $R_4$ is $NO_2$ when $R_2$ is H.

Preferred agents in the classes of Compounds III and IV are glutamyl residue-conjugated analogs of SHPs. In particularly preferred aspects of both of these SHPs, the acid-terminal can be the free acid or its pharmaceutically acceptable salt (preferably, Na). In still other preferred aspects of Compounds IV, $R_7$ can be H or a polyglutamic acid polypeptide residue.

Compounds according to the present invention and especially the preferred compositions according to the present invention, as set forth above, are extremely effective compounds for the treatment of neoplasia. They also exhibit at least one or more improvements such as an enhanced anti-neoplasia activity, a reduced toxicity, a higher water-solubility, or a more favorable pharmacokinetic profile compared to VNP40101 M. Thus, preferred compounds according to the present invention could have a higher therapeutic index (i.e., a better benefit/risk ratio), than VNP40101M.

Compounds according to the present invention may be used in pharmaceutical compositions for the treatment of cancer, as well as a number of other conditions and/or disease states. Examples according to the present invention may be as intermediates in the synthesis of other compounds exhibiting biological activity as well as standards for determining the biological activity of the present compounds. In some applications, the present compounds may be used for treating microbial infections, especially including viral, bacterial, and fungal infections. These compounds comprise an effective amount of any one or more of the compounds disclosed hereinabove, optionally in combination with a pharmaceutically acceptable additive, carrier, or excipient A further aspect of the present invention relates to the treatment of cancer, comprising administering to a patient in need thereof an effective amount of a compound as described hereinabove, optionally in combination with a pharmaceutically acceptable additive, carrier, or excipient. The present invention also relates to methods for treating neoplasia in mammals comprising administering an effective amount of a compound as described hereinabove to a patient suffering from cancer. The treatment of solid malignant tumors, leukemia, and lymphomas comprising administering to a patient an anti-tumor effective amount of one or more these agents is a preferred embodiment of the present invention. The treatment of various other related disease states may also be effected using the compounds of the present invention. This method may also be used in comparison tests such as assays for determining the activities of related analogs as well as for determining the susceptibility of a patient's cancer to one or more of the compounds according to the present invention.

BRIEF DESCRIPTION OF THE FIGURES AND TABLES

DETAILED DESCRIPTION OF THE INVENTION

Figure 1:
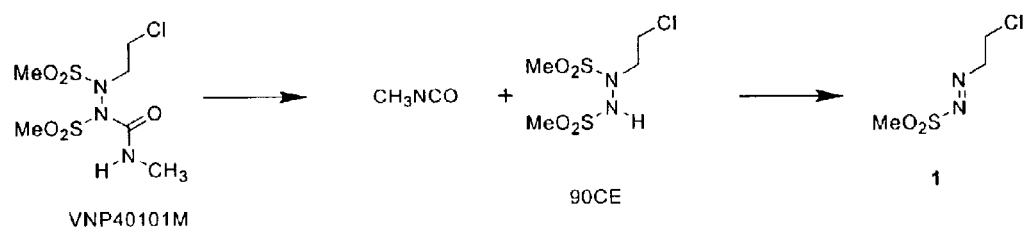
FIG. 1 is a pictorial representation of a suggested mechanism of activation of VNP40101M.

The following terms shall be used throughout the specification to describe the present invention.

The term "patient" is used throughout the specification to describe an animal, including a mammal and preferably a human, to whom treatment, including prophylactic treatment, with the compositions according to the present invention is provided. For treatment of infections, conditions or disease states which are specific for a specific animal such as a human patient, the term patient refers to that specific animal. Preferably, in most aspects of the present invention, patients are human patients.

The term "effective amount" is used throughout the specification to describe concentrations or amounts of compounds according to the present invention which may be used to produce an intended result within its use in context, generally, a favorable change in the disease or condition treated, whether that change is a remission, a decrease in growth or size of cancer or a tumor, a favorable physiological result, a reduction in the growth or elaboration of a tumor, cancerous tissue, or the like, depending upon the disease or condition treated.

The term "neoplasia" is used throughout the specification to describe the pathological process that results in the formation and growth of a neoplasm, i.e., an abnormal tissue that grows by cellular proliferation more rapidly than normal tissue and continues to grow after the stimuli that initiated the new growth cease. Neoplasia could be a distinct mass of tissue that may be benign (benign tumor) or malignant (carcinoma). As used herein, the term neoplasia is used to describe all cancerous disease states and embraces or encompasses the pathological process associated with malignant hematogenous, ascitic, and solid tumors. The term "cancer" and the term "tumor" used in this application is interchangeable with the term "neoplasia".

Cancer which may be treated using compositions according to the present invention include, for example, stomach, colon, rectal, liver, pancreatic, lung, breast, cervix uteri, corpus uteri, ovary, prostate, testis, bladder, renal, brain/CNS, head and neck, throat, Hodgkin's disease, non-Hodgkin's lymphoma, multiple myeloma, melanoma, acute lymphocytic leukemia, acute myelogenous leukemia, Ewing's sarcoma, small cell lung cancer, choriocarcinoma, rhabdomyosarcoma, Wilms' Tumor, neuroblastoma, hairy cell leukemia, mouth/pharynx, oesophagus, larynx, kidney, lymphoma, among others. The treatment of tumors comprising administering to a patient an anti-tumor effective amount of one or more these agents is a preferred embodiment of the present invention.

The term "alkyl" is used throughout the specification to describe a fully saturated hydrocarbon radical containing between one to seven carbon units. Alkyl groups for use in the present invention include linear, branched-chain or cyclic groups, such as preferably methyl, ethyl, propyl, isopropyl, butyl, isobutyl, tert-butyl, pentyl, isopentyl, hexyl, cyclohexyl, methylcyclopropyl and methylcyclohexyl.

The term "salt" is used throughout the specification to describe any salt consistent with the use of the compounds according to the present invention. In the case where the compounds are used in pharmaceutical indications, including the treatment of cancer, the term "salt" shall mean a pharmaceutically acceptable salt, consistent with the use of the compounds as pharmaceutical agents.

The term "glu" or ("Glu") used in chemical formulas according to the present invention refers to a glutamic acid residue or derivative within context which may be bonded on its amino group with another carboxyl group (e.g., RCOOH) or on one of its carboxyl groups with a hydroxyl group or an amino group. Glutamic acid (HOOCCH(NH$_2$)CH$_2$CH$_2$COOH) has two reactive carboxylic acid groups and a reactive amino group, which may be used to form glutamyl residues in compounds according to the present invention. As indicated by the chemical structure, glutamic acid may be bonded on one of the two carboxyl groups with another amino group (RNH$_2$) or a hydroxyl group (ROH) to form the corresponding α-glutamyl or γ-glutamyl amide or ester compound. Alternatively, glutamate may be bonded on its amino group with a carboxyl group forming an N-glutamyl amide derivative. In the present compounds, a single glutamyl residue may be present, as well as a polyglutamyl polypeptide residue, which is a polypeptide formed from two or more glutamate amino acids. The term OCO (Glu) is representative of glutamyl residue (α- or γ-) which is bonded to a free hydroxyl group to form the ester with the α- or γ-carboxylic group (preferably, the α-carboxylic acid group of glutamic acid). The term NHCO(Glu) is representative of a glutamyl residue (α- or γ-) which is bonded to a free amine group to form the amide with the α- or γ-carboxylic group (preferably, the α-carboxylic acid group of glutamic acid). The term "glutamyl" refers to the glutamate amino acid which has been derivatized as an ester or amide. α-glutamyl refers to a glutamate derivative formed at the α-carboxyl group of glutamic acid (ester or amide). γ-glutamyl refers to a glutamate derivative formed at the γ-carboxyl group of glutamic acid (ester or amide). N-glutamyl refers to a glutamate derivative formed at the amino group of glutamic acid (amide). Polyglutamic acid polypeptide residue refers to a polypeptide residue which contains more than one glutamic acid and preferably contains exclusively glutamic acid.

The present invention relates to compounds according to the structure (I):

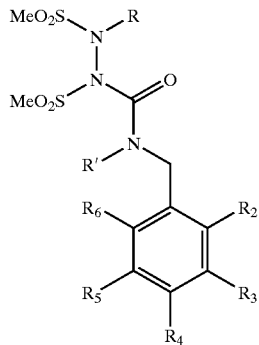

Where

R is —CH$_3$ or —CH$_2$CH$_2$Cl;

R' is C$_1$–C$_7$ alkyl or —CH$_2$CH$_2$Cl; one of R$_2$ or R$_4$, but not both, is selected from OPO$_3$H$_2$, NO$_2$, OCO(Glu), NHCO(Glu) and NHR$_7$ and the other of R$_2$ or R$_4$ which is unassigned, and R$_3$, R$_5$ and R$_6$, are, independently selected from H, F, Cl, Br, I, OH, OPO$_3$H$_2$, OCH$_3$, CF$_3$, OCF$_3$, NO$_2$, CN, SO$_2$CH$_3$, SO$_2$CF$_3$, COCH$_3$, COOCH$_3$, SCH$_3$, SF$_5$, NHR$_8$, N(R$_9$)$_2$, OPO$_3$H$_2$ and C$_1$–C$_7$ alkyl, with the proviso that at least two of R$_2$, R$_3$, R$_4$, R$_5$ and R$_6$ are H;

R$_7$ is H, glutamyl, preferably, α-glutamyl (—COCH(NH$_2$)CH$_2$CH$_2$CO$_2$H) or a polyglutamic acid polypeptide residue —COCH(NHR$_{7a}$)CH$_2$CH$_2$CO$_2$H where R$_{7a}$ is glutamyl (preferably, α-glutamyl) or a polyglutamic acid polypeptide residue having from 1 to 50 peptide linkages, preferably from 2 to 10 peptide linkages;

R$_8$ is H or C$_1$–C$_7$ alkyl; and

R$_9$ is CH$_3$ or CH$_2$CH$_3$. Phosphoric acid and glutamic acid (glutamyl) can be a free acid or a pharmaceutically acceptable salt thereof.

Figure 2:
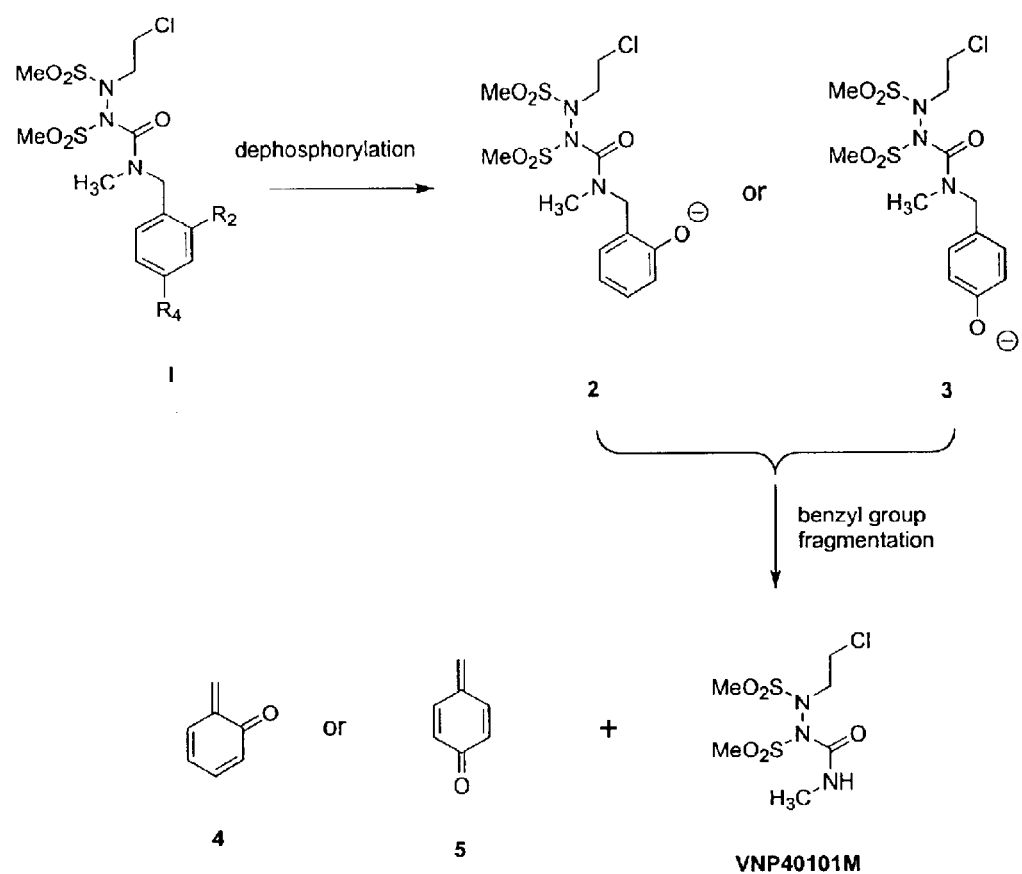
FIGS. 2, 3 and 4 are pictorial representations of the certain chemical embodiments and their proposed mechanisms of activation according to the present invention.
Figure 3:
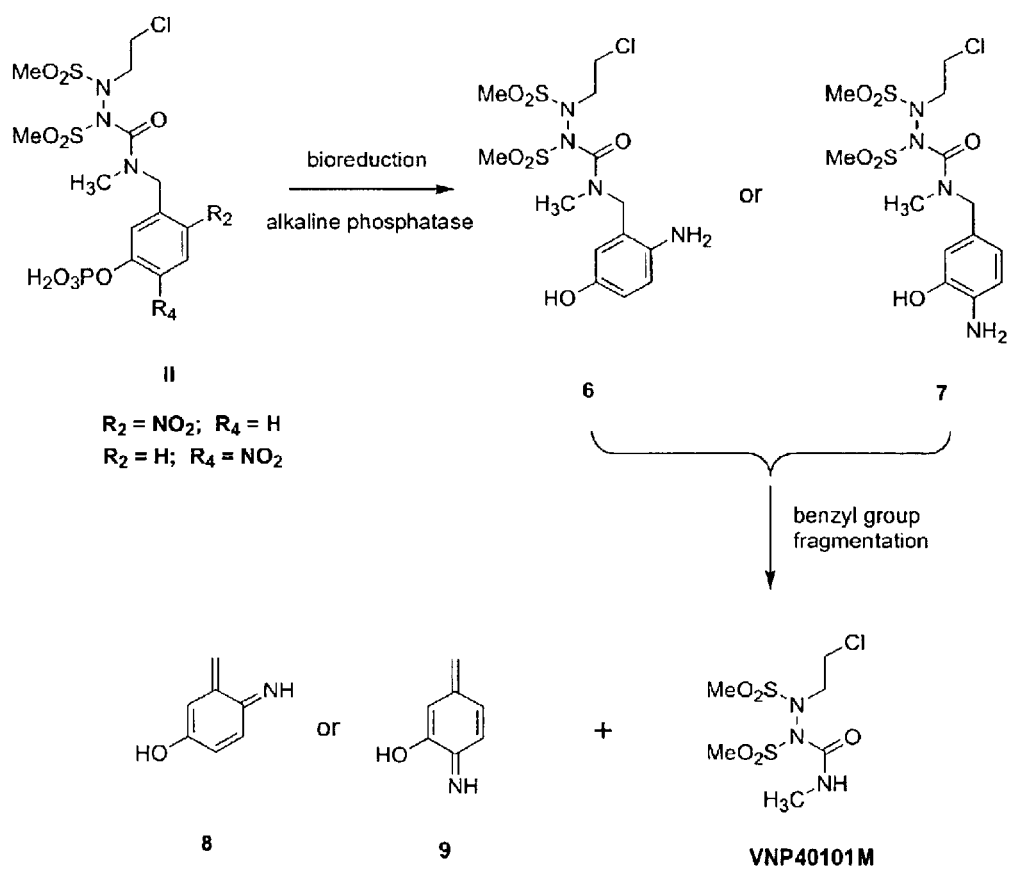
Figure 4:
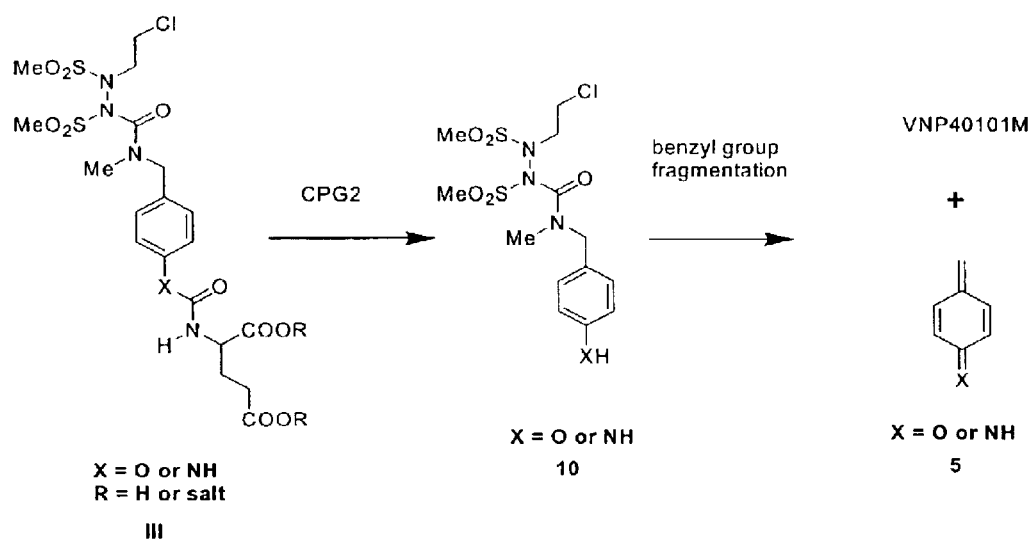
Figure 4:
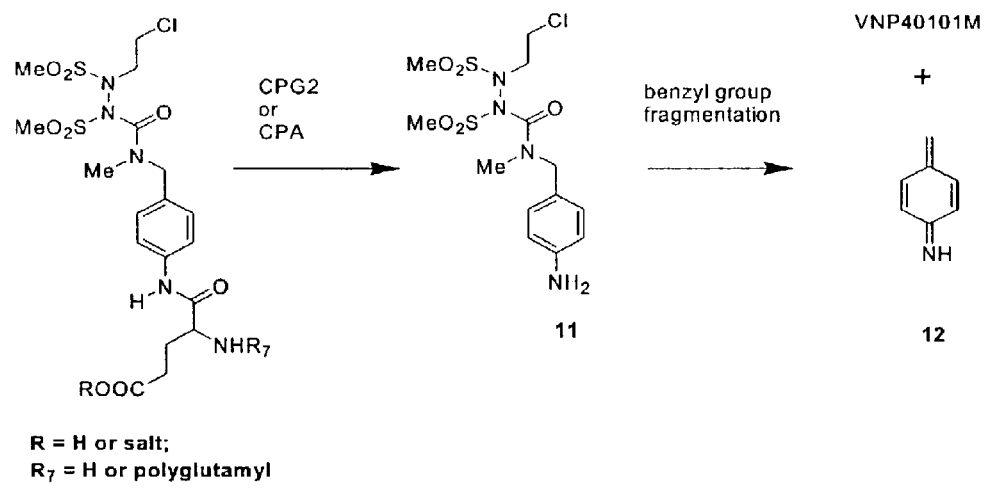

The present compounds represent prodrug forms of intermediates that are believed to exhibit their activity through chloroethylation, methylation, and/or carbamoylation mechanisms, as illustrated in FIGS. 1 to 4. The rationale for the new prodrug design was that enzyme-activated prodrugs could be converted into active alkylating species 1 and methyl isocyanate via a sequence of enzyme activation and prompt fragmentation. For Compounds I, dephosphorylation can be accomplished by the AP enzyme activation to give intermediate 2 or 3 and subsequent benzyl group fragmentation generated the alkylating and carbamoylating species, as shown in FIG. 2. For Compounds II, AP-activated dephosphorylation and NR-activated reduction can afford intermediate 6 or 7, which can generate the alkylating and carbamoylating species via prompt fragmentation, as shown in FIG. 3. For Compounds III and IV, cleavage of the compound can be catalyzed by the CPG2 or CPA enzyme to appropriately substituted phenol 10 and aromatic amine 11, and prompt fragmentation then produces the alkylating and carbamoylating species, as illustrated in FIG. 4.

While not being limited by way of theory, it is theorized that the rate-determining step in this prodrug activation process would appear to be the P—O bond cleavage step, which is catalyzed by the AP enzyme. The subsequent fragmentation step is usually rapid. It is possible that phosphate-linked prodrugs with longer half-lives in circulation, allowing them to act as an active alkylating species depot; or prodrugs with a different distribution than VNP40101M, may have desirable properties. One approach to this goal is to slow down the dephosphorylation step, the rate-limiting step in the bio-activation of the phosphate-bearing SHPs by introducing bulky substituents at the position alpha to the phosphate group. These alkyl groups may impose steric hindrance by the close proximity to the P—O bond cleavage site, thereby slowing down the enzymatic dephosphorylation event. Another approach is to introduce electron-releasing or electron-withdrawing groups in the phenyl ring, which may effect the rate of the P—O bond cleavage. In addition, the subsequent fragmentation step also may be affected by substitution at the phenyl ring with electron-releasing or electron-withdrawing groups. Based upon these considerations, a number of phosphate-bearing SHPs were synthesized readily in good quantities and evaluated. The disodium salts of these prodrugs were very soluble in water.

The compounds according to the present invention are primarily useful for their anti-neoplastic activity, including their activity against solid tumors. In addition, these compositions may also find use as intermediates in the chemical synthesis of other useful anti-neoplastic agents that are, in turn, useful as therapeutic agents or for other purposes.

In preferred Compounds I according to the present invention, R is —CH$_2$CH$_2$Cl; R' is —CH$_3$; R$_2$ is a phosphate group which can be free acid or salt (preferably Na). In particularly preferred aspects of the ortho-phosphate-bearing SHPs, R$_4$ is Cl, F or Br (preferably Cl) when R$_3$, R$_5$ and R$_6$ are H. In other preferred aspects of the ortho-phosphate-bearing SHPs, R$_5$ is Cl, F or Br (preferably Cl, F) when R$_3$, R$_4$ and R$_6$ are H. Still in other preferred aspects of the ortho-phosphate-bearing SHPs, two of R$_3$, R$_4$, R$_5$ and R$_6$ are selected from F, Cl, Br or I (preferably, both substituents are the same and more preferably, both substituents are Cl), the other two of R$_3$, R$_4$, R$_5$ and R$_6$ are H.

In preferred Compounds II according to the present invention, they are meta-phosphate-bearing nitro-containing analogs of SHPs. The phosphate group can be free acid or salt (preferably Na). In particularly preferred aspects of the nitro-containing SHPs, R$_2$ is NO$_2$ when R$_4$ is H. In other preferred aspects of the nitro-containing SHPs, R$_4$ is NO$_2$ when R$_2$ is H.

In preferred Compounds III and IV according to the present invention, they are glutamyl residue-conjugated analogs of SHPs. In particularly preferred aspects of the both SHPs, the acid-terminal can be free acid or salt (preferably Na). Still in preferred aspects of Compounds IV, $R_7$ can be H or polyglutamyl.

Figure 5:
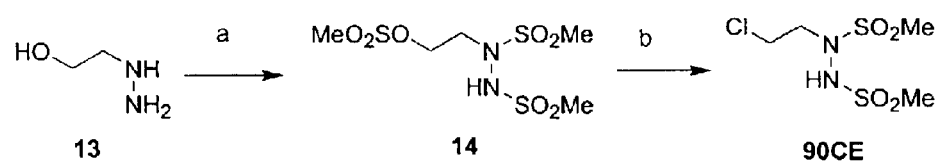
FIGS. 5–9 are pictorial representations of chemical schemes for synthesizing compounds according to the present invention.

Compounds according to the present invention are synthesized by the adaptation of techniques that are well known in the art and are derived from 9OCE. The synthesis of 9OCE is shown in FIG. 5 (see Sartorelli, et al. U.S. Pat. No. 4,684,747, 1987, relevant portions of which are incorporated by reference herein).

Figure 6:
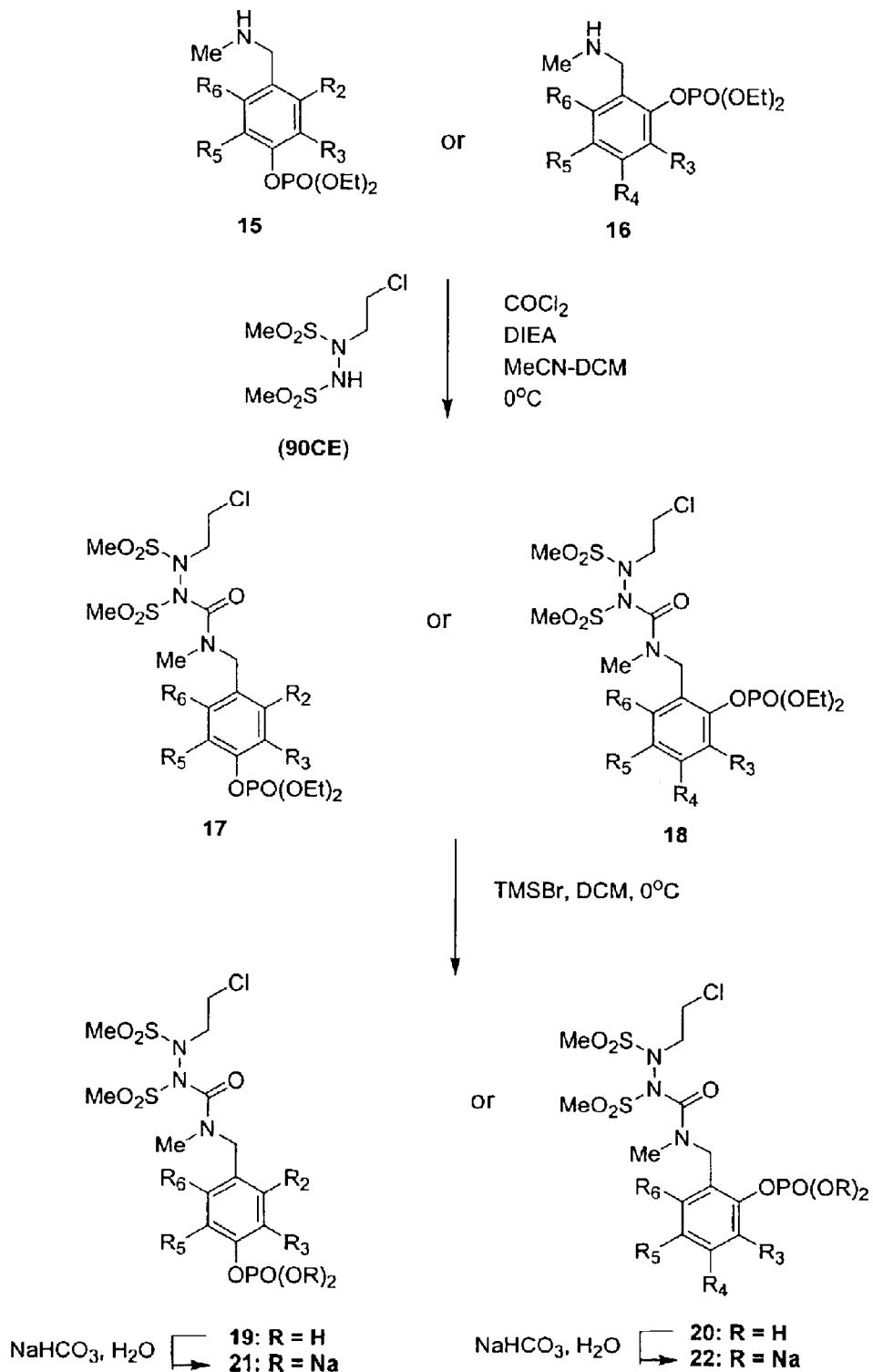

As demonstrated in FIG. 6, 2-aminocarbonyl-1,2-bis (methylsulfonyl)-1-(substituted)hydrazines of Compounds I (19 and 20, R=—$CH_2CH_2Cl$) are synthesized respectively by reacting 9OCE with phosgene or its equivalents, such as triphosgene or trichloromethyl chloroformate (see, Majer, et al. *J Org Chem.* 1994, 59: 1937; and Pridgen, et al. *J Org Chem.* 1989, 54: 3231), and a further condensation in situ with an appropriate N-alkyl-N-benzylamine (15 or 16, where R' is —$CH_3$; $R_2$ or $R_4$ is a phosphate group, such as diethyl phosphonooxy group; and unassigned groups of $R_2$, $R_3$, $R_4$, $R_5$ and $R_6$ are each independently of the indicated structure or a related alkyl group, with the proviso that when any two of unassigned groups of $R_2$, $R_3$, $R_4$, $R_5$ or $R_6$ are other than H, the other two of unassigned groups of $R_2$, $R_3$, $R_4$, $R_5$ or $R_6$ are H). This coupling reaction can be achieved in high yield while using N,N,-diisopropylethylamine (DIEA) as a base and keeping the reaction at 0° C. in dry acetonitrile-dichloromethane solvent overnight. Following deprotection of 17 or 18 with trimethylsilyl bromide (TMSBr) (Matulic-Adamic, et al. *J Org Chem.* 1995, 60: 2563), the phosphate free acid form 19 or 20 is treated with saturated sodium bicarbonate ($NaHCO_3$) solution to afford the corresponding disodium salt 21 or 22, respectively. Reversed phase column chromatography may be employed for purification of the above water-soluble SHPs (19–22).

Figure 7:
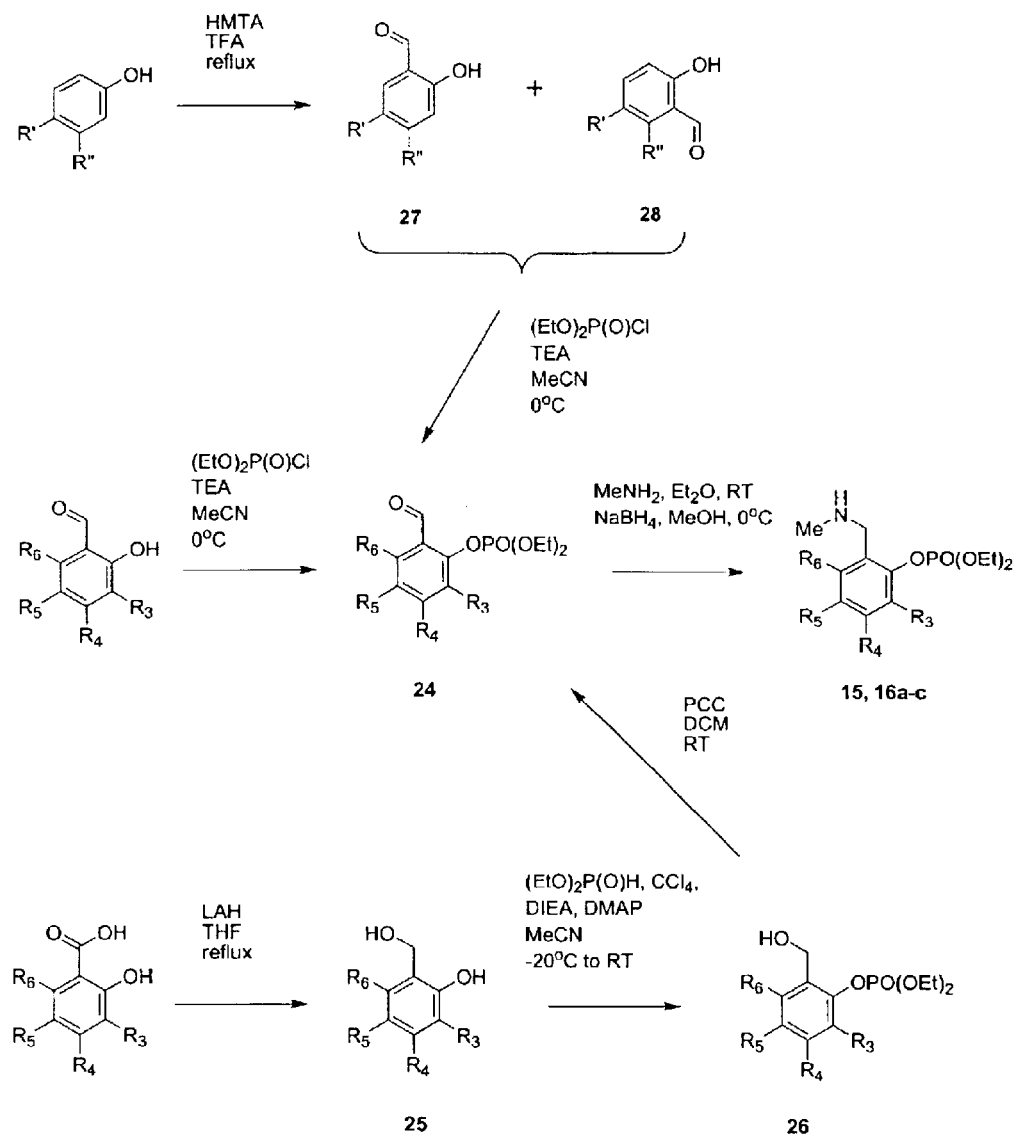

As shown in FIG. 7, the N-benzyl-N-methylamines (15 and 16) can be prepared from the corresponding salicylaldehydes, salicylic acids, or 4-substituted phenols. Commercially available salicylaldehydes react with diethyl chlorophosphate to give their corresponding diethylphosphonoxy-benzaldehydes (23 or 24) under mild conditions. Using sodium borohydride as a reducing agent, the reductive amination of a respective 23 or 24 with methylamine affords the corresponding N-benzylmethylamine (15 or 16). Commercially available salicylic acids are first reduced to the corresponding salicyl alcohols (25) using lithium aluminum hydride (LAH) as a reducing agent at reflux. Selective phosphorylation (Silverberg, et al. *Tetrahedron Lett.* 1996, 37: 771) of the phenol of 25 was acheived with diethyl phosphite, carbon tetrachloride, DIEA and catalytic amounts of 4-dimethylaminopyridine (DMAP) to provide the benzyl alcohols (26). Pyridinium chlorochromate (PCC)-oxidation (Kasmai, et al. *J Org Chem.* 1995, 60: 2267) is used for the transformation of the benzyl alcohols (26) to the benzaldehydes (24). Under Duff formylation conditions using hexamethylene-tetraamine (HMTA) in trifluoroacetic acid (TFA) at reflux (Lindoy, et al., *Synthesis* 1998, 1029), the corresponding salicylaldehydes (27 or 28) were obtained from commercially available 4-subtituted phenols, and then were converted to 24 and 16 via similar phosphorylation and reductive amination steps described above. The synthesis of the appropriate N-alkyl-N-benzylamine derivatives for use in these reaction schemes is well known in the art and uses standard chemical techniques.

Figure 8:
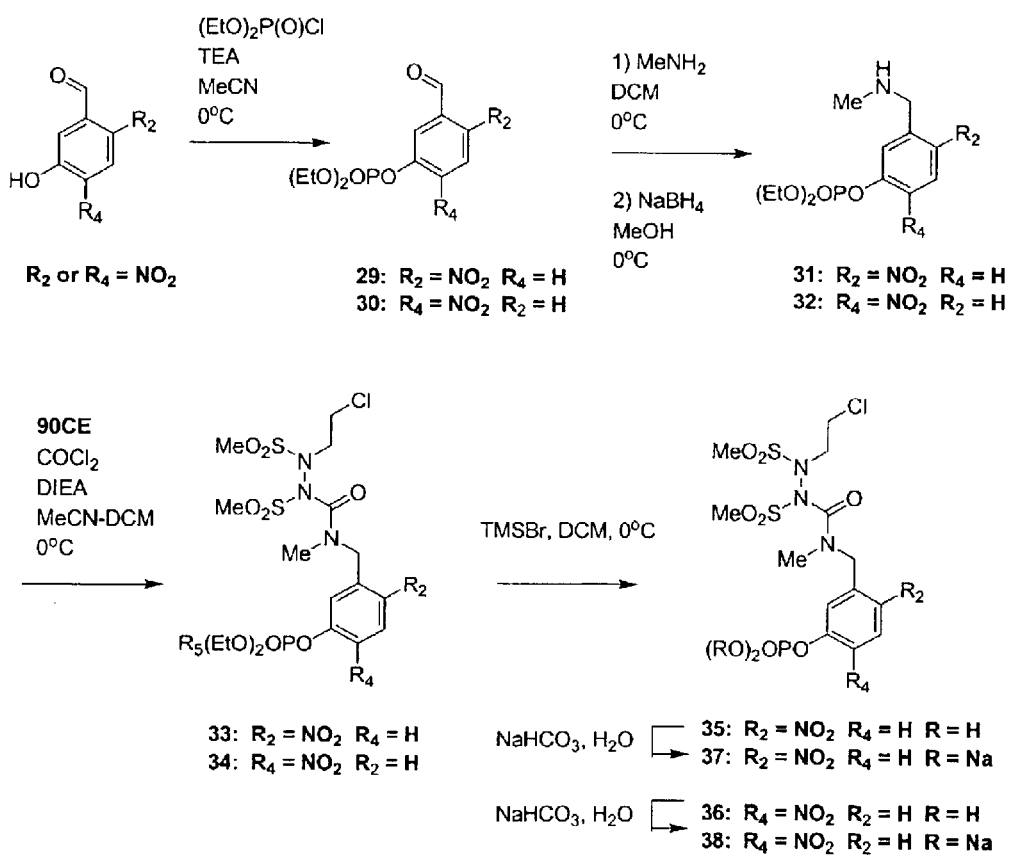

A similar synthetic strategy can also be employed for nitro-containing SHPs of Compounds II, as shown in FIG. 8. Using commercially available nitrobenzaldehydes as the starting material, reaction with diethyl chlorophosphate can give their corresponding diethylphosphonoxy-benzaldehydes (29 or 30) under mild conditions. Using sodium borohydride as a reducing agent, the reductive amination of a respective 29 or 30 with methylamine affords the corresponding nitro-containing N-benzylmethylamine (31 or 32). This coupling reaction of 31 or 32 with 9OCE can be achieved in high yield while using phosgene or its equivalents as a carbonyl coupling agent and DIEA as a base. Following TMSBr-deprotection of 33 or 34, the phosphate free acid form 35 or 36 is treated with saturated $NaHCO_3$ solution to afford the corresponding disodium salt 37 or 38, respectively. Reversed phase column chromatography may be employed for purification of the above water-soluble Compounds II (35–38).

Figure 9:
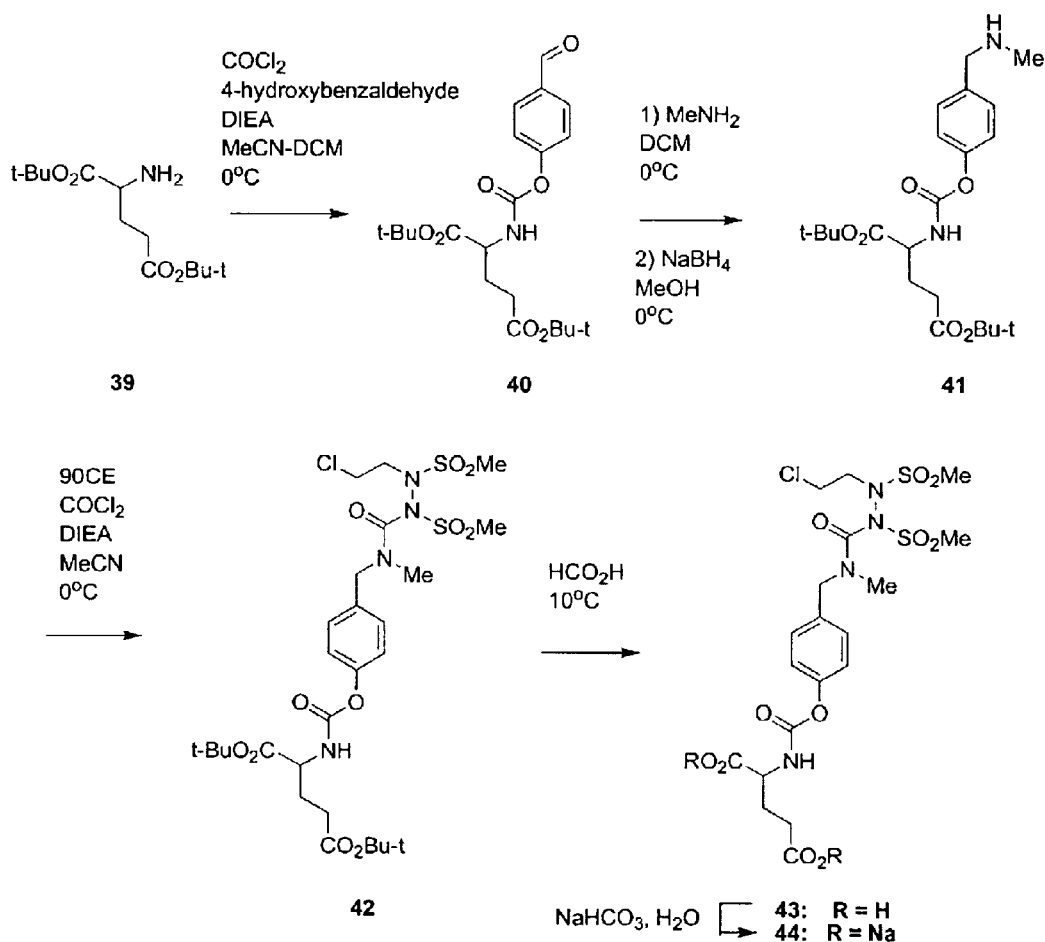

Preparation of the glutamic acid substituted phenols of Compounds III is outlined in FIG. 9. Glutamic acid di-tert-butyl ester (39) reacted with phosgene or its equivalents, followed by condensation in situ with 4-hydroxy-benzaldehyde at 0° C. overnight to give the glutamate-bearing benzaldehyde 40 in good yield. Reductive amination of 40 provided the secondary amine 41 in fair yield. Reaction of compound 41 with phosgene at 0° C., followed by condensation in situ with 9OCE gave 42 successfully. Following a published procedure (Mann, et al. *Tetrahedron* 1990,46: 5377), deprotection of 42 was easily accomplished by treatment with formic acid to afford the free acid 43. Further treatment of 43 with saturated $NaHCO_3$ solution or an appropriate amine can provide a respective water-soluble glutamate 44 such as disodium salt, triethanolamine salt, triethylamine salt, or lutidine salt.

Figure 10:
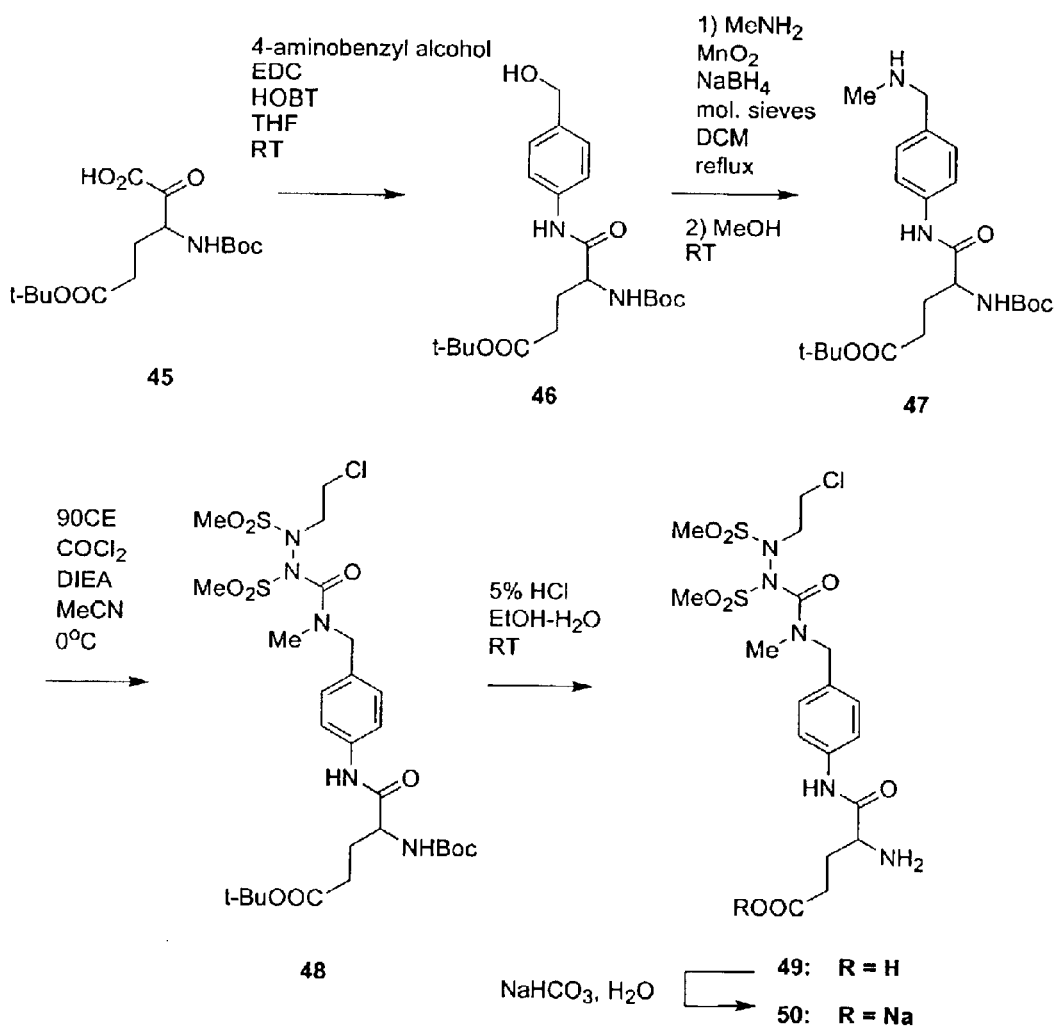
FIGS. 10–15 are pictorial representations of experimental results which are presented in the present application related to the efficacy and toxicity of certain preferred embodiments according to the present invention.

The synthesis of glutamyl substituted aromatic amino analogs (Compounds IV) is illustrated in FIG. 10. Following a literature procedure (Jones, et al. *Bio-org Med Chem Lett.* 2000, 10: 1987), commercially available N-Boc-glutamic acid 5-tert-butyl ester (45) can react with 4-aminobenzyl alcohol to form the amide 46 in high yield, using 1-(3-dimethylaminopropyl)-3-ethylcarbodiimide (EDC) and 1-hydroxybenzotriazole (HOBT) as promoters under mild conditions. As an alternative to prepare a N-benzyl-N-methylamine by PCC-oxidation and reductive amination, a published procedure for the one-pot conversion of the benzyl alcohol 46 into the secondary amine 47 is employed which utilizes manganese dioxide in the presence of sodium borohydride (Kanno, et al. *Tetrahedron Lett.* 2002, 43: 7337). Reaction of the amine 47 with phosgene at 0° C., followed by condensation in situ with 9OCE can generate 48 successfully, using DIEA as promoter. Deprotection of 48 can be easily accomplished by treatment with a dilute hydrochloric acid to afford the free acid 49. Finally, a pharmaceutically acceptable salt, such as sodium salt 50, can be formed after further treatment with saturated $NaHCO_3$ solution.

After synthesis, the crude product generally is purified by reversed phase column chromatography and lyophilization. The synthesis evidences that the SHPs of the present invention may be readily converted to their corresponding phosphate salts. Modification of the disclosed chemical synthetic methods may be readily made by those of ordinary skill in the art in order to provide alternative synthetic pathways to the present compounds.

Pharmaceutical compositions based upon the present novel chemical compounds comprise the above-described compounds in a therapeutically effective amount for the treatment of a condition or disease such as cancer, optionally in combination with a pharmaceutically acceptable additive, carrier or excipient.

Certain of the compounds, in pharmaceutical dosage form, may be used as prophylactic agents for preventing a disease or condition from manifesting itself.

The present compounds or their derivatives can be provided in the form of pharmaceutically acceptable salts. As used therein, the term pharmaceutically acceptable salts or complexes refers to appropriate salts or complexes of the active compounds according to the present invention which retain the desired biological activity of the parent compound. Nonlimiting examples of such salts include the sodium and potassium salts of phosphate and glutamate, among others such as triethanolamine salt, triethylamine salt, lutidine salt, or other pharmaceutically acceptable salts known in the art. Modifications of the active compound can affect the solubility, pharmacokinetic parameters and rate of metabolism of the active species, thus providing control over the delivery of the active species. Further, the modifications can affect the anticancer activity of the compound, in some cases increasing the activity over the parent compound. This can easily be assessed by preparing the derivatives and testing the anticancer activity according to known methods well within the routineer's skill in the art.

The compounds of this invention may be incorporated into formulations for all routes of administration including for example, oral and parenteral, including intravenous, intramuscular, intraperitoneal, intrabuccal, transdermal and in suppository form. Paranteral administration and in particular, intravenous or intramuscular administration is preferred.

Pharmaceutical compositions based upon these novel chemical compounds comprise the above-described compounds in a therapeutically effective amount for treating cancer and other diseases and conditions which have been described herein, optionally in combination with a pharmaceutically acceptable additive, carrier and/or excipient. One of ordinary skill in the art will recognize that a therapeutically effective amount of one of more compounds according to the present invention will vary with the infection or condition to be treated, its severity, the treatment regiment to be employed, the pharmacokinetics of the agent used, as well as the patient (animal or human) treated.

In the pharmaceutical aspect according to the present invention, the compound according to the present invention is formulated preferably in admixture with a pharmaceutically acceptable carrier. In general, it is preferable to administer the pharmaceutical composition parenterally and in particular, in intravenously or intramuscular dosage form, but a number of formulations may be administered via other parenteral routes, such as transdermal, buccal, subcutaneous, suppository or other route, including via an oral route of administration. Intravenous and intramuscular formulations are preferably administered in sterile saline. Of course, one of ordinary skill in the art may modify the formulations within the teachings of the specification to provide numerous formulations for a particular route of administration without rendering the compositions of the present invention unstable or compromising their therapeutic activity. In particular, the modification of the present compounds to render them more soluble in water or other vehicle, for example, may be easily accomplished by minor modifications (such as salt formulation, etc.) which are well within the ordinary skill in the art. It is also well within the routineer's skill to modify the route of administration and dosage regimen of a particular compound in order to manage the pharmacokinetics of the present compounds for maximum beneficial effect to the patient.

The routineer will take advantage of favorable pharmacokinetic parameters of the prodrug forms of the present invention, where applicable, in delivering the present compounds to a targeted site within the host organism or patient to maximize the intended effects of the compound.

Administration of the active compound may range from continuous (intravenous drip), including bolus administration, intravenously or intramuscularly even less frequently than once a day to several administrations per day and may include topical, parenteral, intravenous, intramuscular, subcutaneous, transdermal (which may include a penetration enhancement agent), buccal and suppository administration, among other routes of administration, including, in certain instances, oral administration.

To prepare the pharmaceutical compositions according to the present invention, a therapeutically effective amount of one or more of the compounds according to the present invention is preferably intimately admixed with a pharmaceutically acceptable carrier according to conventional pharmaceutical compounding techniques to produce a dose. A carrier may take a wide variety of forms depending on the form of preparation desired for administration, e.g., intravenous or intramuscular. In preparing pharmaceutical compositions in the appropriate dosage form, any of the usual pharmaceutical media may be used. For parenteral formulations, the carrier may comprise sterile water or aqueous sodium chloride solution in combination with other ingredients that aid dispersion, such as ethanol and other pharmaceutically acceptable solvents, including DMSO, among others. Of course, where solutions are to be used and maintained as sterile, the compositions and carriers must also be sterilized. Injectable suspensions may also be prepared, in which case appropriate liquid carriers, suspending agents and the like may be employed.

Solutions or suspensions used for parenteral, intradermal, subcutaneous, or topical application can be included the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates and agents for the adjustment of tonicity such as sodium chloride or dextrose. The parental preparation can be enclosed in ampoules, disposable syringes or multiple dose vials made of glass or plastic. If administered intravenously, preferred carriers include, for example, physiological saline or phosphate buffered saline (PBS).

In preparing pharmaceutical compositions in oral dosage form, any one or more of the usual pharmaceutical media may be used. Thus, for liquid oral preparations such as suspensions, elixirs and solutions, suitable carriers and additives including water, glycols, oils, alcohols, flavoring agents, preservatives, coloring agents and the like may be used. For solid oral preparations such as powders, tablets, capsules, and for solid preparations such as suppositories, suitable carriers and additives including starches, sugar carriers, such as dextrose, mannitol, lactose and related carriers, diluents, granulating agents, lubricants, binders, disintegrating agents and the like may be used. If desired, the tablets or capsules may be enteric coated or sustained release by standard techniques.

In one embodiment, the active compounds may be prepared with carrier that will protect the compound against rapid elimination from the body, such as a controlled release formulation, including implants and microencapsulated delivery system. Biodegradable, biocompatible polymers can be used, such as ethylene vinyl acetate, polyanhydrides, polyglycolic acid, collagen, polyorthoesters and polyactic acid. Methods for preparation of such formulations will be apparent to those skilled in the art.

Liposomal suspensions may also be pharmaceutically acceptable carriers. These may be prepared according to methods known to those skilled in the art. For example, liposome formulations may be prepared by dissolving appropriate lipid(s) in an inorganic solvent that is then evaporated, leaving behind a thin film of dried lipid on the surface of the container. An aqueous solution of the active compound is then introduced into the container. The container is then swirled by hand to free lipid material from the sides of the container and to disperse lipid aggregates, thereby forming the liposomal suspension. Other methods of preparation well known by those of ordinary skill may be used in this aspect of the present invention.

The present compounds may be used to treat animals, and in particular, mammals, including humans, as patients. Thus, humans, equines, canines, bovines and other animals, and in particular, mammals, suffering from tumors, and in particular, cancer, or other diseases as described herein, can be treated by administering to the patient an effective amount of one or more of the compounds according to the present invention or its derivative or a pharmaceutically acceptable salt thereof optionally in a pharmaceutically acceptable carrier or diluent, either alone, or in combination with other known pharmaceutical agents, depending upon the disease to be treated. This treatment can also be administered in conjunction with other conventional cancer therapies, such as radiation treatment or surgery. In a preferred aspect, the compositions according to the present invention may also be used to treat drug-resistant forms of tumors or cancer, especially those tumors or cancers which are resistant to traditional cancer drugs.

The active compound is included in the pharmaceutically acceptable carrier or diluent in an amount sufficient to deliver to a patient a therapeutically effective amount for the desired indication, without causing serious toxic effects in the patient treated.

The present compounds are prodrug forms of reactive intermediates. In certain pharmaceutical dosage forms, the present compounds may be modified to other prodrug forms to take advantage of a particular route of administration of the active compounds. One of ordinary skill in the art will recognize how to readily modify the present compounds to alternative prodrug forms to facilitate delivery of active compounds to a targeted site within the patient. The individual of ordinary skill also will take advantage of favorable pharmacokinetic parameters of the prodrug forms, where applicable, in delivering the present compounds to a targeted site within the patient to maximize the intended anti-neoplastic effect of the compound.

The amount of compound included within the therapeutically active formulations according to the present invention is an effective amount for treating cancer. In general, a therapeutically effective amount of the compound according to the present invention in dosage form usually ranges from less than about 0.05 mg/kg to about 500 mg/kg of body weight of the patient to be treated, or considerably more, depending upon the compound used, the tumor type to be treated, the ability of the active compound to localize in the tissue to be treated, the route of administration and the pharmacokinetics of the compound in the patient. In the case of treating cancer, the compound is preferably administered in amounts ranging from about 0.05 mg/kg to about 250 mg/kg or more at one time. This dosage range generally produces effective blood level concentrations of active compound ranging from about 0.01 to about 500 micrograms per ml of blood in the patient to be treated. The duration of treatment may be for one or more days or may last for several months or considerably longer (years) depending upon the disease state treated. In a more preferred embodiment, the compound is given to the patient at doses of 0.1 mg/kg to 100 mg/kg, twice per day to once per 14 days, for the duration of 1 week to 52 weeks.

The concentration of active compound in the patient will depend on absorption, distribution, inactivation, and excretion rates of the drug as well as other factors known to those of skill in the art. It is to be noted that dosage given to the patient will be also vary with the severity of the condition to be alleviated. It is to be further understood that for any particular patient, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

The active compound according to the present invention can be also be mixed with other active materials that do not impair the desired action, or with materials that supplement the desired action, such as other anticancer agents, and in certain instances depending upon the desired therapy or target, antibiotics, antifungals, antiinflammatories, or antiviral compounds, among other agents.

Compounds according to the present invention may be administered alone or in combination with other agents, especially including other compounds of the present invention. In these aspects according to the present invention, an effective amount of one or more of the compounds according to the present invention is co-administered along with an effective amount of at lease one additional anti-neoplastic/anticancer agent such as antimetabolites, Ara C, etoposide, doxorubicin, taxol, hydroxyurea, vincristine, cytoxan (cyclophosphamide) or mitomycin C, among numerous others, including topoisomerase I and topoisomerase II inhibitors, such as adriamycin, topotecan, campothecin and irinotecan, other agent such as gemcitabine and agents based upon campothecin and cis-platin. In theory, the present compounds, which act by a mechanism to damage DNA, will act synergistically with compounds that act by a mechanism to reduce or prevent DNA repair. Thus, the present compounds may be advantageously combined with any compound which acts by a mechanism to reduce or prevent DNA repair, especially including inhibitors of enzymes catalyzed DNA repair, such as inhibitors of ribonucleotide reductase (RR) and inhibitors of $O^6$-alkylguanine-DNA alkyltransferase (AGT). By "co-administer" it is meant that the present compounds are administered to a patient such that the present compounds as well as the co-administered compound may be found in the patient's bloodstream at the same time, regardless when the compounds are actually administered, including simultaneously. In many instances, the co-administration of the present compounds with traditional anticancer agents produces a synergistic (i.e., more than additive) result which is unexpected. In another embodiment, the compounds according to the present invention are given either simultaneously or sequentially with antibodies (conjugated or unconjugated), viruses, or bacteria. The antibodies, viruses, or bacteria could carry enzymes or gene encoding enzymes that activate the compounds described in the present invention. The enzymes include but not limit to NR, CPG2 and CPA.

In another aspect of the present invention, the present compositions may be used to treat tumors and/or cancer which are resistant to one or more traditional anti-tumor/anti-cancer agents, such as those which have been described hereinabove. In this aspect of the invention, an effective amount of a composition is administered to a patient suffering from a drug-resistant tumor or cancer in order to treat the tumor or cancer. In this aspect of the present invention, the present compositions may be administered alone or in combination with other effective anti-tumor/anti-cancer agents.

While not being limited by way of theory, it is believed that the compounds according to the present invention primarily induce their therapeutic effect in treating malignant tumors by functional as combined chloroethylating and carbamoylating agents.

Having generally described the invention, reference is now made to the following specific examples that are intended to illustrate preferred and other embodiments and comparisons. The included examples are not to be construed as limiting the scope of this invention as is more broadly set forth above and in the appended claims. Other compounds not specifically presented in the examples section of this application may be readily synthesized following analogous methodologies and/or facile syntheses that are presented and known in the art. One of ordinary skill may readily synthesize all compounds set forth and described without engaging in undue experimentation by simply following the detailed synthetic methodology directly or adapting/modifying such synthetic methodology using techniques well known in the art.

EXAMPLES

All reagents were purchased at commercial quality and used without further purification, and solvents were dried and/or distilled before use where necessary. All NMR spectra ($^1$H, $^{13}$C and $^{31}$P) were determined on a Bruker AC300 spectrometer. Chemical shifts are measured in parts per million (ppm) relative to tetramethylsilane. Coupling constants are reported in Hertz (Hz). Flash column chromatography (FCC) was performed with Merck silica gel 60 (230–400 mesh), and reserved phase column chromatography (RPCC) was packed with CAT gel (Water, preparative C-18, 125 Å, 55–105 $\mu$m) eluting with milli-Q de-ionized water. Electrospray mass (ESMS) analyses were conducted on Q-Tof manufactured by Micromass (Manchester, UK) at Keck Laboratory of Yale University and the mass accuracy could be <0.02%.

Examples 1–3

Preparation of Salicylaldehydes (27a, 27b, 28b) via Formylation of 4-Substituted Phenols (Duff Formylation)

General procedure. To a solution of the appropriately substituted phenol (10.0 g) in TFA (100 mL) was added HMTA (1.1 equivalent) in small portions. The reaction solution was heated at reflux overnight. After cooling, the solution was treated with 50% $H_2SO_4$ solution (40 mL) for 4 h at room temperature, and then was extracted with ether (3×100 mL). The combined ether phases were washed with 5 M HCl solution and water, and then dried over anhydrous $MgSO_4$. After filtration, the filtrate was evaporated and purified.

2-Hydroxy-5-trifluoromethyl-benzaldehyde (27a). Following the general procedure and FCC purification with 30% ethyl acetate-hexane, 4-trifluoromethyl phenol (10.0 g, 61.7 mmol) gave 2-hydroxy-5-trifluoromethyl-benzaldehyde 27 (3.9 g, 34%) as a pink solid.

Rf (20% ethyl acetate-hexane): 0.47.

$^1$H NMR (300 MHz, CDCl$_3$) δ 11.31 (s, 1H, OH), 9.96 (s, 1H, CHO), 7.87 (d, J=1.6 Hz, 1H, C6-H (Ph)), 7.76 (dd, J=2.0 and 8.5 Hz, 1H, C4-H (Ph)) and 7.11 (d, J=8.8 Hz, 1H, C3-H (Ph)).

$^{13}$CNMR (75 MHz, CDCl$_3$) δ 195.8, 163.8, 133.4 (d), 131.0 (d), 125.3, 122.1 (m), 119.8 and 118.6.

4,5-Dichloro-2-hydroxy-benzaldehyde (27b) and 5,6-dichloro-2-hydroxy-benzaldehyde (28). Following the general procedure and FCC purification with 5–10% ethyl acetate-hexane, 3,4-dichlorophenol (10.0 g, 61.1 mmol) gave 5,6-dichloro-2-hydroxy-benzaldehyde 28 (2.2 g, 19%) as a light yellow solid.

Rf (40% ethyl acetate-hexane): 0.63.

$^1$H NMR (300 MHz, CDCl$_3$) δ 11.98 (s, 1H, OH), 10.44 (s, 1H, CHO), 7.55 (d, J=9.4 Hz, 1H, C4-H (Ph)) and 6.89 (d, J=9.3 Hz, 1H, C3-H (Ph)).

$^{13}$C NMR (75 MHz, CDCl$_3$) δ 195.4, 162.4, 137.8 (2C), 135.6, 123.8 and 118.1.

From the same reaction continuous FCC purification with 10% ethyl acetate-hexane gave 4,5-dichloro-2-hydroxy-benzaldehyde 27b (1.8 g, 15%) as a light yellow solid.

Rf (40% ethyl acetate-hexane): 0.47.

$^1$H NMR (300 MHz, CDCl$_3$) δ 10.97 (s, 1H, OH), 9.84 (s, 1H, CHO), 7.64 (s, 1H, C3-H (Ph)) and 7.15 (s, 1H, C6-H (Ph)).

$^{13}$C NMR (75 MHz, CDCl$_3$) δ 194.7, 160.0, 149.9, 141.5, 134.0, 123.6 and 119.9.

Examples 4–6

Preparation of Diethylphosphonoxy-benzaldehydes (23, 24a–b) from Phenolic Aldehydes General procedure. To a stirred ice-cold solution of the appropriately substituted aldehyde (10.0 g) in acetonitrile (120 mL) was added diethyl chlorophosphate (1.1 equivalent) and TEA (1.1 equivalent). The reaction mixture was kept at room temperature overnight. After removal of the precipitate by filtration, the filtrate was evaporated and dried. The crude diethylphosphonoxy-benzaldehyde could be used without further purification.

4-Diethylphosphonoxy-benzaldehyde (23). Following the general procedure, 4-hydroxybenzaldehyde (9.0 g, 73.8 mmol) was converted to 4-diethylphosphonoxy-benzaldehyde 23 (18.9 g, 99%) isolated as a light yellow oil.

$^1$H NMR (300 MHz., CDCl$_3$) δ 9.98 (s, 1H, CHO), 7.91 (d, J=9.0 Hz, 2H, C3-H (Ph)), 7.39 (d, J=8.4 Hz, 2H, C2-H (Ph)), 4.26 (m, 4H, CH$_2$) and 1.38 (t, J=6.9 Hz, 6H, CH$_3$).

$^{13}$C NMR (75 MHz, CDCl$_3$) δ 190.5, 155.2 (d), 133.0, 131.4, 120.3 (d), 64.7 (d) and 15.8 (d).

$^{31}$P NMR (121 MHz, CDCl$_3$) δ 4.6.

TOF ESMS calculated for (M+H)=259.07, observed 259.10.

2-Diethylphosphonoxy-benzaldehyde (24a). Following the general procedure, salicylaldehyde (9.0 g, 73.8 mmol) gave 24a (18.9 g, 99%) as a colorless oil.

$^1$H NMR (300 MHz, CDCl$_3$) δ10.42 (s, 1H, CHO), 7.90 (d, J=7.7 Hz, 1H, C3-H (Ph)), 7.61 (t, J=8.0 Hz, 1H, C5-H (Ph)), 7.48 (d, J=8.7 Hz, 1H, C6-H (Ph)), 7.31 (t, J=7.1 Hz, 1H, C4-H (Ph)), 4.27 (m, 4H, CH$_2$) and 1.37 (t, J=7.1 Hz, 6H, CH$_3$).

$^{13}$C NMR (75 MHz, CDCl$_3$) δ 188.2, 152.5 (d), 135.5, 128.5, 127.1 (d), 125.2, 120.9 (d), 64.9 (d) and 15.8 (d).

$^{31}$P NMR (121 MHz, CDCl$_3$) δ 5.0.

TOF ESMS calculated for (M+H)=259.07, observed 259.07.

5-Chloro-2-diethylphosphonoxy-benzaldehyde (24b). Following the general procedure, 5-chlorosalicylaldehyde (10.0 g, 73.8 mmol) gave 24b (19.4 g, 90%) as a colorless oil.

$^1$H NMR (300 MHz, CDCl$_3$) 610.34 (s, 1H, CHO), 7.84 (d, J=2.5 Hz, 1H, C3-H (Ph)), 7.55 (dd, J=8.8 and 2.5 Hz, 1H, C3-H (Ph)), 7.45 (d, J=8.8 Hz, 1H, C6-H (Ph)), 4.27 (m, 4H, CH$_2$) and 1.38 (t, J=6.8 Hz, 6H, CH$_3$).

$^{13}$C NMR (75 MHz, CDCl$_3$) δ 187.0, 151.1 (d), 135.2, 131.2, 128.2 (d), 128.1, 122.6 (d), 65.2 (d) and 16.0 (d).

$^{31}$P NMR (121 MHz, CDCl$_3$) δ 5.1.

TOF ESMS calculated for (M+H)=293.03, observed 293.04.

Examples 7–9

Preparation of 4-Chloro-2-diethylphosphonoxy-benzaldehyde (24c) from 4-Chlorosalicylic Acid 5-Chloro-2-hydroxymethyl-phenol (25). A solution of 4-chloro salicylic acid (10.0 g, 58.0 mmol) in THF (150 mL) was treated with LAH (1.5 equivalent) at reflux for 2 h. After cooling to ambient temperature, the reaction solution was quenched by 1 N NaHSO$_4$ solution (200 mL), and then extracted with ether (300 mL). After separation, the organic layer was dried over anhydrous MgSO$_4$, filtered and concentrated. The dried crude product 25 (7.5 g, 81%) was obtained as a gray solid, and was pure enough for use without further purification.

$^1$H NMR (300 MHz, DMSO-d6) δ 9.85 (s, 1H, Ph-OH), 7.27 (d, J=8.2 Hz, 1H, C3-H (Ph)), 6.81 (d, J=8.2 Hz, 1H, C4-H (Ph)), 6.78 (s, 1H, C6-H (Ph)), 5.03 (m, 1H, OH) and 4.41 (d, J=4.1 Hz, 2H, PhCH$_2$).

$^{13}$C NMR (75 MHz, DMSO-d6) δ155.0, 131.0, 128.6, 128.0, 118.5, 114.2 and 57.7.

4-Chloro-2-diethylphosphonoxy-benzyl alcohol (26). A solution of 25 (8.6 g, 54.8 mmol), DIEA (2.1 equivalent) and DMAP (0.1 equivalent) in acetonitrile (200 mL) was placed in −20° C. bath. To the above cold solution was added CCl$_4$ (5.0 equivalent) and diethyl phosphite (1.1 equivalent). The reaction solution was kept for 2 h at room temperature. The solvent was rotary evaporated, and the crude oil was purified by FCC with 60% ethyl acetate-hexane to obtain 26 (10.9 g, 68%) as a light yellow oil.

Rf (80% ethyl acetate-hexane): 0.34.

$^1$ NMR (300 MHz, CDCl$_3$) δ 7.40 (d, J=8.2 Hz, 1H, C3-H (Ph)), 7.23 (s, 1H, C6-H (Ph)), 7.19 (d, J=8.5 Hz, 1H, C4-H (Ph)), 4.62 (s, 2H, PhCH$_2$), 4.24 (m, 4H, CH$_2$) and 1.37 (t, J=7.4 Hz, 6H, CH$_3$).

$^{13}$C NMR (75 MHz, CDCl$_3$) δ 148.2 (d), 133.6 (d), 131.6 (d), 131.0, 125.8, 120.9 (d), 65.1 (d), 59.1 and 15.9 (d).

$^{31}$P NMR (121 MHz, CDCl$_3$) δ 6.0.

4-Chloro-2-diethylphosphonoxy-benzaldehyde (24c). To a stirred solution of 26 (10.7 g, 36.3 mmol) in dichloromethane (600 mL) was added PCC in small portions over 30 min at room temperature. The reaction was monitored by TLC. Then, the reaction mixture was passed through a Celite Filter pad, and the filtrate was rotary evaporated. The residual oil was purified by a silica gel pad eluting with ethyl acetate to obtain 24d (9.5 g, 90%) as a green oil.

$^1$H NMR (300 MHz, CDCl$_3$) δ 10.34 (s, 1H, CHO), 7.84 (s, 1H, C3-H (Ph)), 7.52 (s, 1H, C6-H (Ph)), 7.29 (s, 1H, C4-H (Ph)), 4.29 (m, 4H, CH$_2$) and 1.39 (s, 6H, CH$_3$).

$^{13}$C NMR (75 MHz, CDCl$_3$) δ 186.8, 152.4(d), 140.9, 129.3, 125.4(d), 125.3, 121.1, 64.9 (d) and 15.6 (d). $^{31}$P NMR (121 MHz, CDCl$_3$) δ 4.8.

TOF ESMS calculated for (M+H)=293.03, observed 293.06.

Examples 10–13

Preparation of N-(Diethylphosphonoxybenzyl)N-methylamines (15, 16a–c)

General Procedure. To a solution of the corresponding diethylphosphonoxy-benzaldehyde (23 or 24a–c, 10 mmol) in dichloromethane (10 mL) was added methylamine (2 N in THF, 2.0 equivalent). The reaction solution was kept at room temperature overnight, filtered through a silica gel pad, the filtrate was rotary evaporated and dried in vacuum. The resulting crude oil was dissolved in methanol (50 mL). To the above solution was added NaBH$_4$ (2.0 equivalent) in small portions at 0° C., and the solution was kept stirring continuously for 4 h. After evaporation, the residue was distributed in water (50 mL) and dichloromethane (50 mL). The aqueous phase was separated and extracted with dichloromethane (50 mL) once. The combined organic phases were dried over anhydrous MgSO$_4$, filtered and evaporated. The crude N-(diethylphosphonoxybenzyl)-N-methylamines (15 or 16a–c) was pure enough for use without further purification.

N-(4-Diethylphosphonoxybenzyl)-N-methyl amine (15). Following the general procedure, 23 (29.9 g, 116 mmol) gave 15 (22.3 g, 71%) as a yellow oil.

$^1$H NMR (300 MHz, CDCl$_3$) δ 7.31 (d, J=8.0 Hz, 2H, C3-H (Ph)), 7.17 (d, J=8.5 Hz, 2H, C2-H (Ph)), 4.21 (m, 4H, CH$_2$), 3.73 (s, 2H, PhCH$_2$), 2.42 (s, 3H, NCH$_3$) and 1.34 (t, J=6.9 Hz, 6H, CH$_3$).

$^{13}$C NMR (75 MHz, CDCl$_3$) δ 149.4 (d), 135.6, 129.3, 119.5 (d), 64.2 (d), 54.5, 35.1 and 15.7 (d).

$^{31}$P NMR (121 MHz, CDCl$_3$) δ 5.3.

TOF ESMS calculated for (M+H)=274.11, observed 274.11.

N-(2-Diethylphosphonoxybenzyl)-N-methyl amine (16a). Following the general procedure, 24a (19.0 g, 73.6 mmol) gave 16a (16.4 g, 82%) as a light yellow oil.

$^1$H NMR (300 MHz, CDCl$_3$) δ 7.37 (d, J=7.4 Hz, 1H, C3-H (Ph)), 7.33 (d, J=7.9 Hz, 1H, C6-H (Ph)), 7.24 (t, J=7.2 Hz, 1H, C5-H (Ph)), 7.14 (t, J=7.3 Hz, 1H, C4-H (Ph)), 4.22 (m, 4H, CH$_2$), 3.82 (s, 2H, PhCH$_2$), 2.44 (s, 3H, NCH$_3$) and 1.35 (t, J=7.0 Hz, 6H, CH$_3$).

$^{13}$C NMR (75 MHz, CDCl$_3$) δ 148.6 (d), 130.5 (d), 130.2, 128.1, 124.8, 119.7, 64.4 (d), 49.9, 35.5 and 15.8 (d).

$^{31}$P NMR (121 MHz, CDCl$_3$) δ 5.6.

TOF ESMS calculated for (M+H)=274.11, observed 274.13.

N-(4-Chloro-2-diethylphosphonoxybenzyl)-N-methyl amine (16b). Following the general procedure, 24b (21.9 g, 74.9 mmol) gave 16b (18.3 g, 80%) as a light yellow oil.

$^1$H NMR (300 MHz, CDCl$_3$) δ 7.39 (d, J=2.2 Hz, 1H, C3-H (Ph)), 7.27 (d, J=7.9 Hz, 1H, C6-H (Ph)), 7.20 (dd, J=8.3 and 2.6 Hz, 1H, C5-H (Ph)), 4.23 (m, 4H, CH$_2$), 3.78 (s, 2H, PhCH$_2$), 2.45 (s, 3H, NCH$_3$) and 1.36 (t, J=7.0 Hz, 6H, CH$_3$).

$^{13}$CNMR (75 MHz, CDCl$_3$)δ 147.1 (d), 132.8(d), 130.1 (d), 129.7, 127.7, 121.1, 64.6(d), 49.6, 35.6 and 15.9 (d).

$^{31}$P NMR (121 MHz, CDCl$_3$) δ 5.6.

TOF ESMS calculated for (M+H)=308.07, observed 308.08.

N-(5-Chloro-2-diethylphosphonoxybenzyl)N-methyl amine (16c). Following the general procedure, 24c (23.9 g, 81.7 mmol) gave 16c (18.9 g, 76%) as a light yellow oil.

$^1$H NMR (300 MHz, CDCl$_3$) δ 7.35 (s, 1H, C6-H (Ph)), 7.30 (d, J=10.4 Hz, 1H, C3-H (Ph)), 7.14 (d, J=8.4 Hz, 1H, C4-H (Ph)), 4.24 (m, 4H, CH$_2$), 3.78 (s, 2H, PhCH$_2$), 2.43 (s, 3H, NCH$_3$) and 1.37 (t, J=6.8 Hz, 6H, CH$_3$).

$^{13}$C NMR (75 MHz, CDCl$_3$) δ 140.9 (d), 133.0, 131.0, 129.4 (d), 125.1, 120.3 (d), 64.7 (d), 49.4, 35.5 and 15.9 (d).

$^{31}$P NMR (121 MHz, CDCl$_3$) δ 5.4.

TOF ESMS calculated for (M+H)=308.07, observed 308.08.

Examples 14–15

Preparation of Free Phosphonic Acids (19, 20a–c)

General Procedure. To a cold stirred solution of 90CE (10 mmol) in acetonitrile (40 mL) was added phosgene (20% in toluene, 1.0 equivalent) and DIEA (1.0 equivalent). The reaction solution was kept at 0° C. for 20 min. Then, to the above solution was added a solution of the corresponding N-(diethylphosphonoxy-benzyl)-N-methylamine (15 or 16a–c, 10 mmol) in dichloromethane (5 mL) and DIEA (another 1.0 equivalent). The final reaction solution was kept at 5° C. overnight. After evaporation, the residue was distributed in water (80 mL) and dichloromethane (80 mL). The aqueous phase was separated and extracted with dichloromethane (80 mL) twice. The combined organic phases were dried over anhydrous MgSO$_4$, filtered and evaporated. The crude protected phosphates (17 or 18a–c) were obtained as oils.

A solution of the respective diethyl-protected phosphate (17 or 18a–c, 10 mmol) in dichloromethane (60 mL) was treated with excess TMSBr (40 mL) at 5° C. overnight. After evaporation and drying in vacuum, the crude free phosphoric acid (19 or 20a–c) was obtained as a glassy solid.

To the crude compound (19 or 20a, 10 mmol) was added water (about 30 mL). The suspension was stirred for 2 h at ambient temperature, and then a minimum amount of water was added to complete dissolution. The aqueous solution was purified by RPCC with de-ionized water. The fractions were monitored by $^{31}$P NMR and combined. After lyophylization, the purified free phosphoric acid (19 or 20a) was obtained as a white powder.

1,2-Bis(methylsulfonyl)-1-(2-chloroethyl)-hydrazine (90CE). Following a published procedure (Shyam, et al. *J Med Chem.* 1987, 30: 2157), the reaction of 2-hydroxyethyl-hydrazine and methanesulfonyl chloride in the presence of pyridine as a base provided the mesylate, which subsequently reacted with lithium chloride to result in 90CE. 90CE was obtained as a white solid after purification by FCC with 5% methanol in dichloromethane.

Rf (50% ethyl acetate-hexane): 0.30.

$^1$H NMR (300 MHz, CDCl$_3$) δ 6.82 (s, 1H, NH), 3.99 (t, J=6.8 Hz, 2H, ClCH$_2$), 3.86 (t, J=5.6 Hz, 2H, NCH$_2$), 3.19 (s, 3H, SCH$_3$) and 3.13 (s, 3H, SCH$_3$).

$^{13}$C NMR (75 MHz, CDCl$_3$) δ 54.0, 41.0, 40.2 and 38.4.

Phosphoric acid mono-{4-{N-[1,2-bis(methylsulfonyl)-2-(2-chloroethyl)-hydrazinylcarbonyl]-N-methylaminomethyl}-phenyl} ester (19). Following the general procedure, 15 (15.4 g, 56.8 mmol) and 90CE (14.2 g, 1.0 equivalent) gave phosphoric acid 4-{N-[1,2-bis(methylsulfonyl)-2-(2-chloroethyl)-hydrazinylcarbonyl]-N-methylaminomethyl}-phenyl ester diethyl ester (17, 25.2 g, 80%). Compound 17 (11.0 g, 20.1 mmol) was converted to 19 (3.8 g, 38%) as a white powder.

$^1$H NMR (300 MHz, D$_2$O) δ 7.11 (d, J=8.1 Hz, 2H, C3-H (Ph)), 6.95 (d, J=7.5 Hz, 2H, C2-H (Ph)), 4.36 (m, 2H, PhCH$_2$), 3.89 (m, 2H, ClCH$_2$), 3.67 (m, 2H, NCH$_2$), 3.23 (s, 3H, NCH$_3$), 2.92 (s, 3H, SCH$_3$) and 2.87 (s, 3H, SCH$_3$).

$^{13}$C NMR (75 MHz, D$_2$O) δ 156.6, 153.8 (d), 133.4, 132.0, 123.0 (d), 57.3, 55.7, 43.6, 42.0, 40.4 and 39.1.

$^{31}$P NMR (121 MHz, D$_2$O) δ 9.9.

TOF ESMS calculated for (M+H)=494.01, observed 493.98.

Phosphoric acid mono-{2-{N-[1,2-bis(methylsulfonyl)-2-(2-chloroethyl)-hydrazinylcarbonyl]-N-methylaminomethyl}-phenyl} ester (20a). Following the general procedure, 16a (16.4 g, 60.5 mmol) and 90CE (15.1 g, 1.0 equivalent) gave phosphoric acid 2-{N-[1,2-bis(methylsulfonyl)-2-2-chloroethyl)-hydrazinylcarbonyl]-N-methylaminomethyl}-phenyl ester diethyl ester (18a, 29.7 g, 89%). Compound 18a (10.5 g, 19.2 mmol) gave 20a (2.6 g, 27%) as a white powder.

$^1$H NMR (300 MHz, D$_2$O) δ 7.1–7.2 (m, 3H, C3-H, C5-H and C6-H (Ph)), 6.94 (m, 1H, C4-H (Ph)), 4.45 (m, 2H, PhCH$_2$), 3.84 (m, 2H, ClCH$_2$), 3.64 (m, 2H, NCH$_2$), 3.20 (s, 3H, NCH$_3$), 2.93 (s, 3H, SCH$_3$) and 2.92 (s, 3H, SCH$_3$).

$^{13}$C NMR (75 MHz, D$_2$O) δ 156.8, 152.5 (d), 131.8, 131.7, 128.7 (d), 126.7, 122.5, 57.2, 51.4, 43.5, 42.1, 40.5 and 39.9.

$^{31}$P NMR (121 MHz, D$_2$O) & 9.8.

TOF ESMS calculated for (M+H)=494.01, observed 494.00.

Examples 16–19

Preparation of the Disodium Salts (21, 22a–c)

General Procedure. The corresponding crude phosphoric acid (19 or 20a–c, 10 mmol) was neutralized with an aqueous saturated sodium bicarbonate (NaHCO$_3$) solution (100 mL). The suspension was stirred for 2 h at ambient temperature, and then added to a minimum amount of water to make homogenous. The aqueous solution was purified by RPCC with de-ionized water. The fractions were monitored by $^{31}$P NMR and combined. After lyophylization, the corresponding disodium salt (21 or 22a–c) was obtained as a white powder.

Phosphoric acid 4-{N-[1,2-bis(methylsulfonyl)-2-(2-chloroethyl)-hydrazinylcarbonyl]-N-methylaminomethyl}-phenyl ester disodium salt (21). Following the general procedure, crude 19 (9.5 g, 19.3 mmol) gave 21 (5.6 g, 54%) as a white powder.

$^1$H NMR (300 MHz, D$_2$O) δ 7.08 (d, J=8.3 Hz, 2H, C3-H (Ph)), 6.97 (d, J=8.1 Hz, 2H, C2-H (Ph)), 4.38 (m, 2H, PhCH$_2$), 3.92 (m, 2H, ClCH$_2$), 3.71 (m, 2H, NCH$_2$), 3.26 (s, 3H, NCH$_3$), 2.95 (s, 3H, SCH$_3$) and 2.89 (s, 3H, SCH$_3$).

$^{13}$C NMR (75 MHz, D$_2$O) δ 156.5, 156.1 (d), 131.7, 131.4, 122.9 (d), 57.4, 55.8, 43.7, 42.0, 40.5 and 39.0.

$^{31}$P NMR (121 MHz, D$_2$O) δ 14.2.

TOF ESMS calculated for (M−H)=492.01, observed 492.10.

Phosphoric acid 2-{N-[1,2-bis(methylsulfonyl)-2-(2-chloroethyl)-hydrazinylcarbonyl]-N-methylaminomethyl}-phenyl ester disodium salt (22a). Following the general procedure, crude 20a (8.8 g, 17.8 mmol) gave 22a (5.7 g, 59%) as a white powder.

$^1$H NMR (300 MHz, D$_2$O) δ 7.21 (d, J=8.4 Hz, 1H, C3-H (Ph)), 7.0–7.2 (m, 2H, C5-H and C6-H (Ph)), 6.86 (t, J=7.2 Hz, 1H, C4-H (Ph)), 4.52 (m, 2H, PhCH$_2$), 3.90 (m, 2H, ClCH$_2$), 3.68 (m, 2H, NCH$_2$), 3.27 (s, 3H, NCH$_3$), 2.97 (s, 3H, SCH$_3$) and 2.93 (s, 3H, SCH$_3$).

$^{13}$C NMR (75 MHz, D$_2$O) δ 156.7, 154.6 (d), 131.3, 130.9, 128.3 (d), 124.7, 122.4, 57.3, 51.4, 43.6, 42.0, 40.5 and 39.9.

$^{31}$P NMR (121 MHz, D$_2$O) δ14.1.

TOF ESMS calculated for (M–H)=492.01, observed 492.05.

Phosphoric acid 2-{N-[1,2-bis(methylsulfonyl)-2-(2-chloroethyl)-hydrazinyl-carbonyl]-N-methylaminomethyl}-4-chloro-phenyl ester disodium salt (22b). Following the general procedure, crude 20b (14.5 g, 27.6 mmol) gave 22b (8.3 g, 53%) as a white powder.

$^1$H NMR (300 MHz, D$_2$O) δ7.26 (s, 1H, C3-H (Ph)), 7.17 (m, 1H, C5-H (Ph)), 7.08 (d, J=7.2 Hz, 1H, C6-H (Ph)), 4.48 (m, 2H, PhCH$_2$), 3.93 (m, 2H, ClCH$_2$), 3.72 (m, 2H, NCH$_2$), 3.30 (s, 3H, NCH$_3$), 3.03 (s, 3H, SCH$_3$) and 3.01 (s, 3H, SCH$_3$).

$^{13}$C NMR (75 MHz, D$_2$O) δ156.8, 153.3 (d), 134.6, 130.8, 128.9, 126.7, 123.6, 57.3, 51.3, 43.6, 42.1, 40.6 and 40.1.

$^{31}$P NMR (121 MHz, D$_2$O) δ14.2.

TOF ESMS calculated for (M–H)=525.96, observed 525.93.

Phosphoric acid 2-{N-[1,2-bis(methylsulfonyl)-2-(2-chloroethyl)-hydrazinyl-carbonyl]-N-methylaminomethyl}-s-chloro-phenyl ester disodium salt (22c). Following the general procedure, crude 20c (16.2 g, 30.8 mmol) gave 22c (8.9 g, 51%) as a white powder.

$^1$H NMR (300 MHz, D$_2$O) δ 7.28 (s, 1H, C6-H (Ph)), 7.03 (d, J=8.4 Hz, 1H, C3-H (Ph)), 6.87 (d, J=8.2 Hz, 1H, C4-H (Ph)), 4.47 (m, 2H, PhCH$_2$), 3.91 (m, 2H, ClCH$_2$), 3.70 (m, 2H, NCH$_2$), 3.26 (s, 3H, NCH$_3$), 3.00 (s, 3H, SCH$_3$) and 2.96 (s, 3H, SCH$_3$).

$^{13}$C NMR (75 MHz, D$_2$O) δ156.7, 155.3 (d), 135.6, 132.0, 127.0 (d), 124.5, 122.4, 57.3, 51.0, 43.7, 42.0, 40.5 and 40.0.

$^{31}$P NMR (121 MHz, D$_2$O) δ14.1.

TOF ESMS calculated for (M–H)=525.96, observed 526.01.

Example 20

Preparation of the Carbamate (40)

4-Formylphenyloxycarbonyl-glutamic acid di-tert-butyl ester (40). To a cold stirred solution of 4-hydroxybenzyl alcohol (2.0 g, 16.9 mmol) in acetonitrile (50 mL) and dichloromethane (50 mL) was added phosgene (20% in toluene, 1.0 equivalent) and DIEA (1.0 equivalent). The reaction solution was kept at 0° C. for 30 min. Next, to the above solution was added a solution of glutamic acid di-tert-butyl ester 39 (1.0 equivalent) in dichloromethane (50 mL) including DIEA (2.0 equivalent). The reaction mixture was kept at 0° C. overnight. Then, the mixture was treated with 0.5 N KHSO$_4$ solution (50 mL). After separation, the organic phase was washed with brine (80 mL), dried over anhydrous MgSO$_4$, rotary evaporated and dried in vacuum. The crude carbamate 40 (6.7 g, 97%) was obtained as a light yellow semi-solid.

$^1$H NMR (300 MHz, CDCl$_3$) δ 9.97 (s, 1H, CHO), 7.89 (d, J=8.1 Hz, 2H, C3-H (Ph)), 7.32 (d, J=8.7 Hz, 2H, C2-H (Ph)), 5.91 (d, J=7.8 Hz, 1H, NH), 4.32 (m, 1H, C$^1$H), 2.35 (m, 2H, C2H), 2.00 (m, 2H, C$^3$H), 1.50 and 1.46 (s, 2×9H, CH$_3$).

$^{13}$C NMR (75 MHz, CDCl$_3$) δ 191.0, 172.1, 170.6, 155.6, 153.1, 133.4, 131.1, 121.9, 82.7, 80.9, 54.1, 31.4, 28.0, 27.9 and 27.5.

TOF ESMS calculated for (M+H)=408.20, observed 408.19.

Example 21

Preparation of the N-Benzyl-N-methylamine (41)

4-(Methyaminomethyl)phenyloxycarbonyl-glutamic acid di-tert-butyl ester (41). A stirred solution of 40 (6.1 g, 14.9 mmol) in dichloromethane (50 mL) was treated with 2 N methylamine-THF solution (10 mL) at 0° C. overnight. After removal of solvents, the residual oil was dissolved in methanol (80 mL) and placed in an ice-bath. To the above solution was added sodium borohydride in small portions over 30 min. The reaction solution was kept at 0° C. for 1 hour, and solvent was then evaporated. The residue was worked up with brine and dichloromethane. After separation, the organic phase was dried over anhydrous MgSO$_4$, rotary evaporated and dried in vacuum. The crude amine 41 (5.4 g, 78%) was obtained as a light yellow glassy solid.

$^1$H NMR (300 MHz, CDCl$_3$) δ 7.04 (d, J=8.3 Hz, 2H, C3-H (Ph)), 6.78 (d, J=8.1 Hz, 2H, C2-H (Ph)), 5.36 (d, J=7.4 Hz, 1H, CONH), 4.39 (m, 1H, C$^1$H), 2.86 (d, J=4.6 Hz, 3H, NCH$_3$), 2.74 (d, J=4.8 Hz, 2H, NCH$_2$), 2.34 (m, 2H, C$^2$H), 1.92 (m, 2H, C$^3$H), 1.49 and 1.42 (s, 2×9H, CH$_3$).

$^{13}$CNMR (75 MHz, CDCl$_3$)δ 172.6, 172.4, 157.9, 156.1, 128.6, 128.3, 115.6, 82.0, 80.7, 53.9, 51.5, 33.8, 31.6, 28.0, 27.9 and 27.6.

TOF ESMS calculated for (M+H)=423.25, observed 423.24.

Example 22

Preparation of the N-Benzyl-N-methylaminocarbonyl-hydrazine (42)

4-{N-(1,2-Bis(methylsulfonyl)-1-(2-chloroethyl) hydrazin-2-yl-carbonayl)N-methyaminomethyl}phenyloxycarbonyl-glutamic acid di-tert-butyl ester (42). To a cold stirred solution of 90CE (1.5 g, 5.9 mmol) in acetonitrile (30 mL) was added phosgene (20% in toluene, 1.0 equivalent) and DIEA (1.0 equivalent). The reaction solution was kept at 0° C. for 30 min. Then, to the above solution was added a solution of 41 (1.0 equivalent) in acetonitrile (30 mL) including DIEA (1.0 equivalent). The reaction mixture was kept at 0° C. overnight. After evaporation of solvent, the resulting residue was worked up with water and dichloromethane. After separation, the organic phase was dried over anhydrous MgSO$_4$, rotary evaporated and dried in vacuum. The crude N-benzyl-N-methylaminocarbonyl-hydrazine 42 (3.6 g, 87%) was obtained as a light yellow glassy solid.

$^1$H NMR (300 MHz, CDCl$_3$) δ7.31 (d, J=8.0 Hz, 2H, C3-H (Ph)), 7.21 (d, J=8.2 Hz, 2H, C2-H (Ph)), 5.38 (d, J=7.5 Hz, 1H, CONH), 4.52 (bs, 1H, C$^1$H), 3.82 (m, 2H, ClCH$_2$), 3.67 (m, 2H, NCH$_2$), 3.55 (s, 3H, NCH$_3$), 3.23 and 3.14 (s, 2×3H, SO$_2$CH$_3$), 2.87 (s, 2H, NCH$_2$Ph), 2.35 (m, 2H, C$^2$H), 1.98 (m, 2H, C$^3$H), 1.47 and 1.43 (s, 2×9H, CH$_3$).

$^{13}$C NMR (75 MHz, CDCl$_3$) δ172.7, 172.1, 157.6, 148.8, 137.0, 128.9, 128.7, 121.0, 81.7, 80.5, 53.8, 53.4, 51.2, 41.9, 41.7, 41.3, 40.4, 31.5, 27.9, 27.8 and 27.4.

TOF ESMS calculated for (M+H)=699.21, observed 699.18.

Example 23

Preparation of the Glutamic Acid (43) and Its disodium Salt (44)

4-{N-(1,2-Bis(methylsulfonyl)-1-(2-chloroethyl)hydrazin-2-yl-carbonayl)-N-methyaminomethyl}phenyloxycarbonyl-glutamic acid (42) and its disodium salt (44). The crude glassy solid 42 (4.4 g, 6.4 mmol) was treated with formic acid (200 mL) at 5° C. overnight. After frozen at −78° C., the desired glutamic acid 43 was obtained by lyophylization as sticky white solid.

Without further purification, crude 43 was treated with saturated $NaHCO_3$ solution (200 mL) at room temperature for 2 hours. The resulting milky mixture was purified by RPFCC with de-ionized water. The fractions were monitored by HPLC and combined. After lyophylization, the disodium salt 44 (0.78 g, 20%) was obtained as a white powder.

$^1$H NMR (300 MHz, $D_2O$) δ 7.15 (d, J=8.0 Hz, 2H, C3-H (Ph)), 7.08 (d, J=7.8 Hz, 2H, C2-H (Ph)), 4.31 (bs, 1H, C$^1$H), 3.83 (m, 2H, ClCH$_2$), 3.67 (m, 2H, NCH$_2$), 3.46 (s, 3H, NCH$_3$), 3.16 (s, 3H, SO$_2$CH$_3$), 2.95 (m, 2H, NCH$_2$Ph), 2.70 (s, 3H, SO$_2$CH$_3$), 1.99 (m, 2H, C$^2$H) and 1.75 (m, 2H, C$^3$H).

$^{13}$C NMR (75 MHz, $D_2O$) δ 185.0, 182.7, 162.0, 154.4, 150.8, 140.0, 131.0, 123.6, 59.1, 55.1, 53.5, 43.7, 42.9, 36.7, 36.4 and 31.2.

TOF ESMS calculated for (M+H)=631.05, observed 631.04, and for (M+Na)=653.03, observed 653.03.

Example 24

Determination of Solubility and Stability in Aqueous Solutions

The solubility of VNP401101M in water is 0.66 mg/mL at room temperature (Krishna, et al. *AAPS PharmsciTech* 2001, 2: article 14). The solubility of the newly synthesized SHPs (19, 20a, 21, and 22a) is much higher than that of VNP40101 M, as shown in Table 1.

For the free phosphoric acid 19 and 20a, an excess amount of the drug was placed in a glass vial containing 2.0 mL of water. The vials were shaken in a Glas Col rotary apparatus at room temperature for 24 hours. The suspension containing undissolved drug was centrifuged; the supernatant was carefully separated and analyzed by HPLC for drug concentration. The solubility of 19 and 20a was found to be 293 and 46 mg/mL respectively. Aqueous solutions of 19 and 20a were colorless. Similarly, the solubility of the sodium salts 21 and 22a was determined visually by adding incremental quantities of the drug to 2.0 mL of water in a glass vial. The vials were shaken at room temperature in a Glas Col rotary apparatus until the drug dissolved entirely. Additional fixed quantities of drug were added and the vials shaken until complete dissolution. This process was continued until no more drug dissolved. Compounds 21 and 22a are highly water-soluble. Because of limited drug supplies determination of the solubilities at equilibrium could not be obtained. Solubilities of >0.98 and >1.35 g/mL for 21 and 22a, respectively, were determined.

TABLE 1

Water-solubility of the Projected SHPs at Room Temperature

| Compound | Water-solubility, mg/mL |
| --- | --- |
| VNP40101M | 0.66 |
| PAP-101M (19) | 293 |
| OAP-101M (20a) | 46 |
| PAP-Na-101M (21) | >980 |
| OAP-Na-101M (22a) | >1350 |

The stabilities of PAP-101M (19), OAP-101M (20a), and VNP40101M were investigated in potassium phosphate buffers (50 mM) at pH 3, 5, 7 and 9 and at room temperature (22–25° C.). One sample was prepared at each pH for each drug; the initial drug concentration in each sample was 50 μg/mL. Each sample was analyzed by HPLC repetitively, at various time points, to determine the

TABLE 2

Aqueous Stability of the Projected SHPs

| | Half-life | | | |
| --- | --- | --- | --- | --- |
| Compound | pH 3 | pH 5 | pH 7 | pH 9 |
| VNP40101M | No hydrolysis | 118 day | 12.2 hr | 6.9 min |
| PAP-101M (19) | No hydrolysis | No hydrolysis | No hydrolysis | No hydrolysis |
| OAP-101M (20a) | No hydrolysis | No hydrolysis | No hydrolysis | 171 day | concentration of the respective drug. The first-order kinetic half-lives of each drug were calculated. As demonstrated in Table 2 below, the results indicate clearly that the phosphate-bearing prodrugs (19 and 20a) were quite stable compared to VNP40101M.

Example 25

Determination of In Vitro Bioconversion and Stability

Table 3 shows the bioconversion of compounds 19 and 20a in the presence of AP (from bovine intestinal mucosa, Sigma) or human plasma. Each drug, at a final concentration of approximately 50 μg/mL, was incubated at 37° C. in 50 mM Tris buffered saline (pH 7.6) containing approximately 0.055 unit/mL of the phosphatase enzyme.

TABLE 3

In vitro Enzymatic Bioconversion and Human Plasma Stability

| | Half-life, min | | |
| --- | --- | --- | --- |
| Compound | Alkaline phosphatase 37° C. | Human plasma 37° C. | Buffered saline pH 7.6 37° C. |
| VNP40101M | Not tested | 14.5 | 20.5 |
| PAP-101M (19) | 21.1 | 34.3 | No hydrolysis |
| OAP-101M (20a) | 29.0 | 53.3 | No hydrolysis |

A control sample of each drug at a final concentration of 50 μg/mL in 50 mM Tris buffered saline (pH 7.6) without AP was also incubated at 37° C. Aliquots of each solution were taken periodically; disappearance of the tested drug was determined by HPLC.

The stability of compounds 19, 20a and VNP40101M was evaluated in 100% human plasma (pooled mixed gender, BioChemed) at a final concentration of 50 μg/mL. Each drug (19 or 20a) was incubated in human plasma at 37° C. for a maximum of two hours. Aliquots of the incubation mixture were taken at various time points and extracted with acetonitrile. The extract was separated by centrifugation and analyzed directly by HPLC. In a similar manner, VNP40101M was incubated in human plasma at 37° C. for a maximum of one hour. At various time points, aliquots of the incubation mixture were removed and extracted with 0.5% $H_3PO_4$ in acetonitrile. The extract was separated by centrifugation and analyzed directly by HPLC. For comparison, the stability of each drug incubated in 50 mM Tris buffered saline (pH 7.6) instead of 100% human plasma was also determined.

It is clearly shown that (a) the projected prodrugs 19 and 20a were more stable in buffered saline and human plasma than VNP40101M; and (b) they could be rapidly activated by alkaline phosphatase. OAP-101M (20a) was shown to have a longer half-life than PAP-101M (19).

Example 26

Pharmacokinetic Study In Rats

Preliminary investigations of the pharmacokinetic profiles of prodrugs 19 and 20a were conducted in female Sprague-Dawley rats (10 weeks old, 250 g, Charles River). Each prodrug was administered as a single bolus intravenous (iv) injection via the jugular vein at a dose of 50 mg per kg (mpk) of body weight. Blood samples were collected on the day of dosing at the following time points: pre-dose and approximately 2, 10, 30 min, 1, 2, and 24 hr, after dosing. At each time point, approximately 0.2 mL of blood was collected in a tube containing an anticoagulant (heparin), which was immediately acidified by adding 0.005 mL of a 2.0 M citric acid solution. Then, the tube was inverted 4 to 6 times and immediately placed on ice. The blood samples were centrifuged within 30 min after blood collection at 3,000 rpm for 10–20 min at 2–8° C., and the plasma fraction was transferred to a labeled Nunc cryovial. The plasma samples were immediately frozen on dry ice and stored at −20° C. until HPLC-UV analysis. Animals were euthanized with $CO_2$ inhalation after experiments.

Bioanalytical methods were developed to quantify these prodrugs in rat plasma using HPLC-UV at either 220 nm or 230 nm. Each plasma sample (0.1 mL) was extracted with 0.2 mL of acetonitrile. The extract was separated by centrifugation and analyzed directly by HPLC-UV. HPLC calibration standards were prepared in control rat plasma and processed as above. The standard curve had a linear range of 1.0–50 μg/mL.

Determination of 19 could not be done because of the fast conversion or clearance of the compound from the circulation of rats. As demonstrated in Table 4, pharmacokinetic parameters (area under the concentration-time curve— AUC, total body clearance—Cl, steady-state volume of distribution—Vss, maximum concentration—Cmax, and terminal half-life—$T_{1/2}$) were calculated. Plasma half-life for 20a was approximately 14 min, which was longer than that of 19. Comparison to VNP101M (10 mpk of radioactive VNP101M was used in previous experiments) is difficult because of the difference in doses used in two the studies.

TABLE 4

Pharmacokinetic Parameters of 19 and 20a in Rats

| Drug | AUC (min*ug/ mL) | Cl (mL/min/ kg) | Vss (mL/kg) | Cmax (μg/mL) | $T_{1/2}$ (min) |
|---|---|---|---|---|---|
| 19 | — | — | — | — | — |
| 20a | 1312.0 | 37.8 | 145.6 | 238.6 | 14.0 |
| VNP40101M* | 325.8 ± 113.8 | 2.0 ± 0.6 | 0.91 ± 0.16 | 11.3 ± 2.1 | 20.9 ± 8.7 |

*The plasma VNP40101M level (~10 μg/mL) peaked at 2 min after administration of [$^{14}$C]-VNP40101M. The VNP40101M levels declined, with a half-life of ~20 min. After the first 2 hours, no VNP40101M could be detected in the plasma (see, Almassian, et al. Proceedings AACR, 2001, 42: 326, article 1756).

Example 27

Evaluation of in Vivo Anti-tumor Activity

Figure 11:
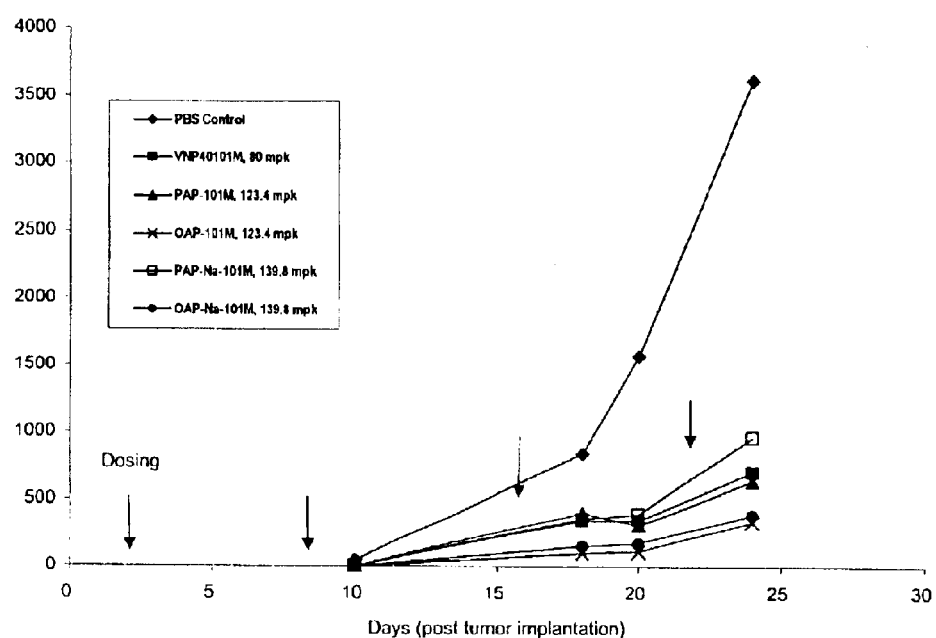
Figure 12:
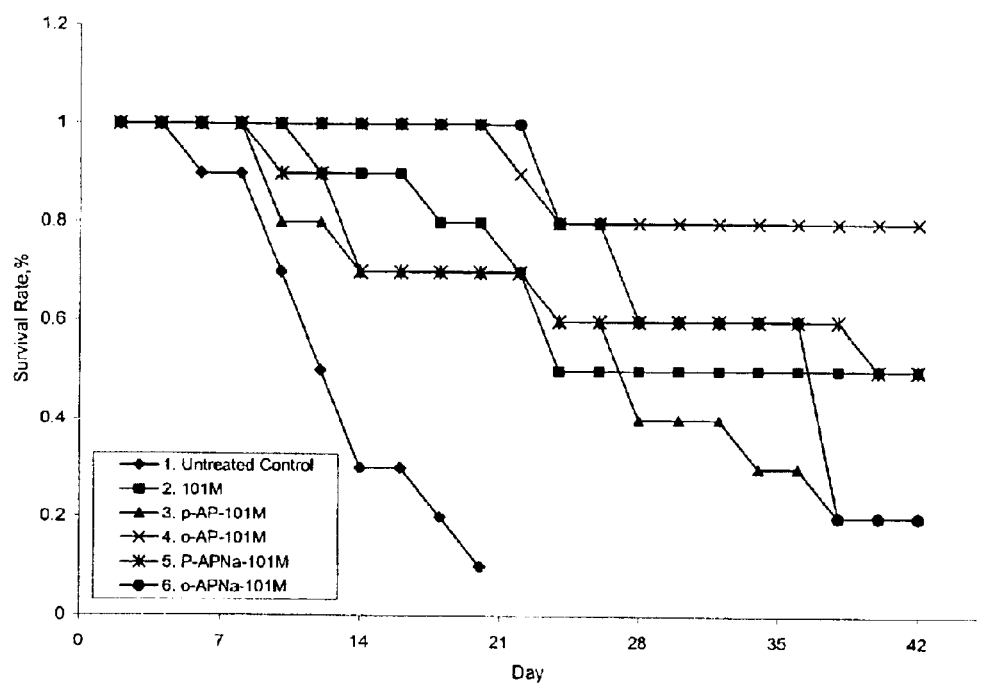
Figure 13:
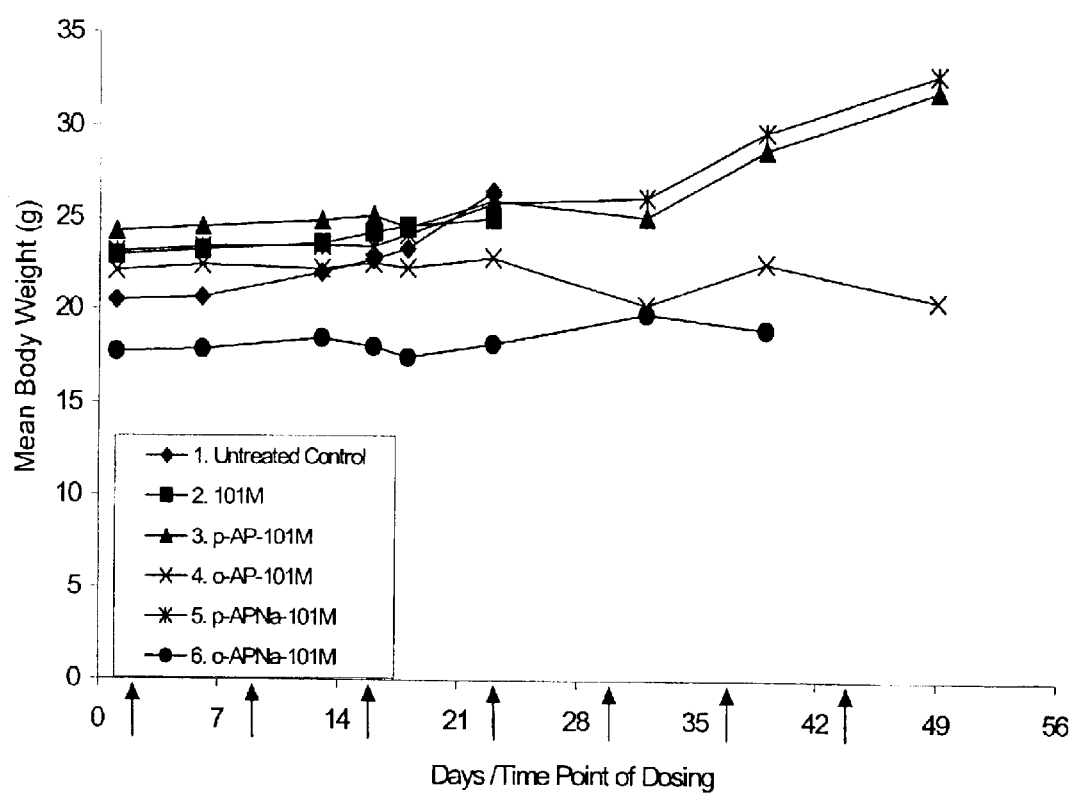
Figure 14:
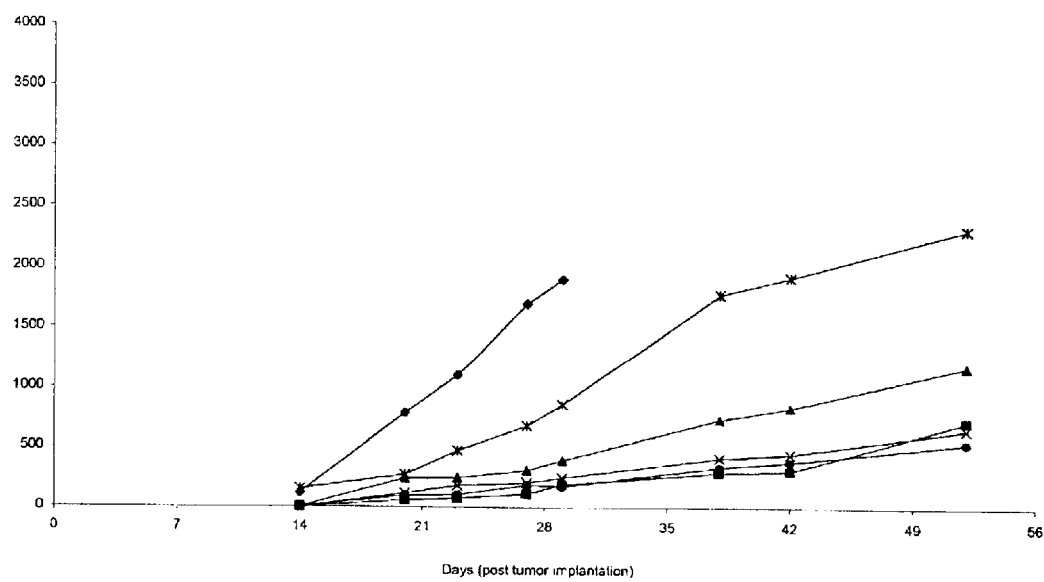
Figure 15:
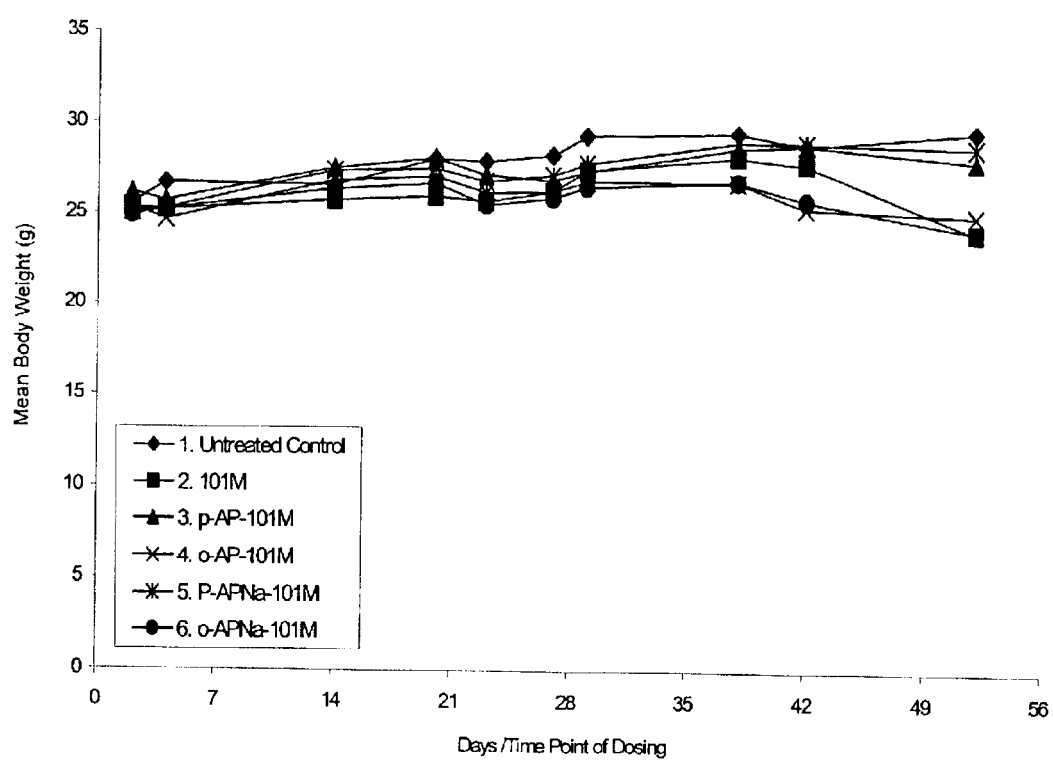

The anti-tumor effects of VNP40101 M and prodrugs, including PAP-101M (19), OAP-101M (20a), PAP-Na-101M (21), and OAP-Na-101M (22a), were evaluated in both the B16-F10 murine melanoma and HTB177 human lung carcinoma models. B16-F10 melanoma cells were implanted subcutaneously (5×10$^5$ cells) into C57BL/6 mice, which were randomized into groups of ten immediately after tumor cell implantation (Day 0). On Day 2, mice were injected intraperitoneally with either a bolus injection of 0.1 mL PBS or drug. The treatment was carried out weekly for four consecutive weeks. Tumor measurement in three dimensions was determined once a week with the formula L×H×W/2, where L, H, and W represent length, height, and width, respectively. As shown in FIG. 11, B16-F10 tumors in the PBS control group grew exponentially, reaching a size around 4,000 mm$^3$ on Day 24. VNP40101M and tested prodrugs effectively inhibited the growth of B16-F10 melanoma. On Day 24, tumor growth was inhibited by 81% in mice treated with 80 mg/kg of VNP40101M, and by 75 to 91% in mice treated with equal molar doses of the prodrugs. Of all the prodrugs, OAP-101M (20a) and OAP-Na-101M (22a) were the most efficacious; tumor growth inhibitions were 91% and 89.5%, respectively. The inhibitions were significantly (p<0.05) higher than those in others groups. Tumor-bearing mice receiving OAP-101 M (20a) also survived longer than that received other drugs (FIG. 12). The toxicity of these drugs in mice was mild as determined by body weight loss and animal appearance, as illustrated in FIG. 13. The anti-tumor effects of these prodrugs had also been investigated in HTB177 human lung carcinoma implanted in nu/nu CD-1 mice, as demonstrated in FIGS. 14 and 15, and been shown that OAP-101M (20a) and OAP-Na-101M (22a) holdout promise as well.

In short, we have shown that the water-soluble SHP prodrugs OAP-101M (20a) and OAP-Na-101M (22a) have anti-tumor activity against the B16-F10 murine melanoma and HTB177 human lung carcinoma and the efficacy was as good as or better than VNP40101M.

SUMMARY

In summary, phosphate-bearing SHPs OAP-101M (20a) and OAP-Na-101 M (22a) possesses the following characteristics: (a) highly water-soluble and stable in aqueous solution at pH 3 to 9; (b) its conversion can be catalyzed by alkaline phosphatase (AP); (c) has longer half-life in saline and in human plasma than PAP-101 M (19) and VNP40101M; (d) has better in vivo PK profiles than PAP-101M; (e) has good anti-tumor activities against B16-F10 murine melanoma and HTB177 human lung carcinoma in mice as compared to PAP-101M (19), PAP-Na-101M (21) and VNP40101M; and (f) its sodium salt (22a) has even a higher water-solubility and similar anti-tumor activity than the free acid 20a.

It is to be understood by those skilled in the art that the foregoing description and examples are illustrative of practicing the present invention, but are not in no way limiting. Variations of the detail presented herein may be made without departing from the spirit and scope of the present invention as defined by the following claims.

We claim:

1. A compound or its pharmaceutically acceptable salt of the structure:

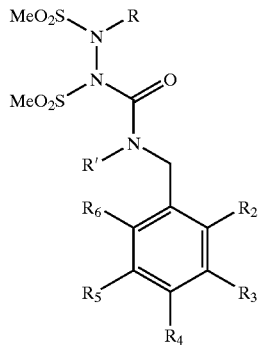

Where

R is —CH$_3$ or —CH$_2$CH$_2$Cl;

R' is C$_1$–C$_7$ alkyl or —CH$_2$CH$_2$Cl; one of R$_2$ or R$_4$, but not both, is selected from OPO$_3$H$_2$, NO$_2$, OCO(Glu), NHCO(Glu) and NHR$_7$ and the other of R$_2$ or R$_4$ which is unassigned, and R$_3$, R$_5$ and R$_6$, are, independently selected from H, F, Cl, Br, I, OH, OPO$_3$H$_2$, OCH$_3$, CF$_3$, OCF$_3$, NO$_2$, CN, SO$_2$CH$_3$, SO$_2$CF$_3$, COCH$_3$, COOCH$_3$, SCH$_3$, SF$_5$, NHR$_8$, N(R$_9$)$_2$ and C$_1$–C$_7$ alkyl, with the proviso that at least two of R$_2$, R$_3$, R$_4$, R$_5$ and R$_6$ are H;

R$_7$ is H, glutamyl or a polyglutamic acid polypeptide residue —OCH(NHR$_{7a}$)CH$_2$CH$_2$CO$_2$H where R$_{7a}$ is glutamyl or a polyglutamic acid polypeptide residue having from 1 to 50 peptide linkages;

R$_8$ is H or C$_1$–C$_7$ alkyl; and

R$_9$ is CH$_3$ or CH$_2$CH$_3$.

2. The compound according to claim 1 wherein R is —CH$_2$CH$_2$Cl.

3. The compound according to claim 1 wherein said R' is methyl, ethyl, n-propyl, isopropyl, n-butyl, isobutyl, t-butyl, n-pentyl, isopentyl, n-hexyl, isohexyl or substituted hexyl.

4. The compound according to claim 3 wherein R' is methyl.

5. The compound according to claim 1 wherein R$_2$ is a OPO$_3$H$_2$ group or its pharmaceutically acceptable salt.

6. The compound according to claim 1 wherein R$_4$ is F, Cl or OCH$_3$ when R$_3$, R$_5$ and R$_6$ are each H.

7. The compound according to claim 1 wherein R$_5$ is F, Cl, OCH$_3$ or OCF$_3$ when R$_3$, R$_4$ and R$_6$ are each H.

8. The compound according to claim 1 wherein two of R$_3$, R$_4$, R$_5$ or R$_6$ are independently F or Cl.

9. The compound according to claim 8 wherein R$_4$ and R$_5$ are independently F or Cl.

10. The compound according to claim 8 wherein R$_5$ and R$_6$ are independently F or Cl.

11. The compound according to claim 9 wherein R$_4$ and R$_5$ are Cl.

12. The compound according to claim 10 wherein R$_5$ and R$_6$ are Cl.

13. The compound according to claim 1 wherein R$_5$ is a OPO$_3$H$_2$ group or its pharmaceutically acceptable salt.

14. The compound according to claim 1 wherein R$_2$ is NO$_2$ and R$_3$, R$_4$ and R$_6$ are each H.

15. The compound according to claim 1 wherein R$_4$ is NO$_2$ and R$_2$, R$_3$ and R$_6$ are each H.

16. The compound according to claim 1 wherein R$_4$ is OCO(Glu) and R$_2$, R$_3$, R$_5$ and R$_6$ are each H.

17. The compound according to claim 16 wherein OCO(Glu) is in the form of a pharmaceutically acceptable salt.

18. The compound according to claim 1 wherein R$_4$ is NHCO(Glu) and R$_2$, R$_3$, R$_5$ and R$_6$ are each H.

19. The compound according to claim 18 wherein NHCO(Glu) is in the form of a pharmaceutically acceptable salt.

20. The compound according to claim 1 wherein R$_4$ is NHR$_7$ and R$_2$, R$_3$, R$_5$ and R$_6$ are each H.

21. The compound according to claim 20 wherein R$_7$ is H, a α-glutamyl or a pharmaceutically acceptable salt thereof or a polyglutamic acid polypeptide residue having from 1 to 50 peptide linkages or a pharmaceutically acceptable salt thereof.

22. The compound according to claim 21 wherein R$_7$ is α-glutamyl or a pharmaceutically acceptable salt thereof or a polyglutamic acid polypeptide residue having from 2 to 10 peptide linkages or a pharmaceutically acceptable salt thereof.

23. A pharmaceutical composition comprising an effective amount for treating a tumor of a compound or its pharmaceutically acceptable salt according to the structure:

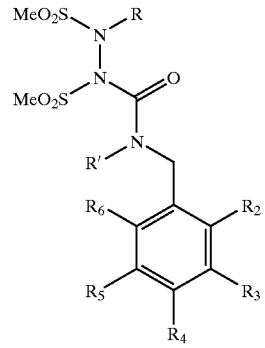

Where

R is —CH$_3$ or —CH$_2$CH$_2$Cl;

R' is C$_1$–C$_7$ alkyl or —CH$_2$CH$_2$Cl;

one of R$_2$ or R$_4$, but not both, is selected from OPO$_3$H$_2$, NO$_2$, OCO(Glu), NHCO(Glu) and NHR$_7$ and the other of R$_2$ or R$_4$ which is unassigned, and R$_3$, R$_5$ and R$_6$, are, independently selected from H, F, Cl, Br, I, OH, OPO$_3$H$_2$, OCH$_3$, CF$_3$, OCF$_3$, NO$_2$, CN, SO$_2$CH$_3$, SO$_2$CF$_3$, COCH$_3$, COOCH$_3$, SCH$_3$, SF$_5$, NHR$_8$, N(R$_9$)$_2$ and C$_1$–C$_7$ alkyl, with the proviso that at least two of R$_2$, R$_3$, R$_4$, R$_5$ and R$_6$ are H;

R$_7$ is H, glutamyl or a polyglutamic acid polypeptide residue (—COCH(NHR$_{7a}$)CH$_2$CH$_2$CO$_2$H where R$_{7a}$ is glutamyl or a polyglutamic acid polypeptide residue having from 1 to 50 peptide linkages;

R$_8$ is H or C$_1$–C$_7$ alkyl; and

R$_9$ is CH$_3$ or CH$_2$CH$_3$; optionally, in combination with a pharmaceutically acceptable additive, carrier, or excipient.

24. The composition according to claim 23 wherein R is —CH$_2$CH$_2$Cl.

25. The composition according to claim 23 wherein said R' is methyl, ethyl, n-propyl, isopropyl, n-butyl, isobutyl, t-butyl, n-pentyl, isopentyl, n-hexyl, isohexyl or substituted hexyl.

26. The composition according to claim 25 wherein R' is methyl.

27. The composition according to claim 23 wherein R$_2$ is OPO$_3$H$_2$ or its pharmaceutically acceptable salt.

28. The composition according to claim 23 wherein R$_4$ is F, Cl or OCH$_3$ when R$_3$, R$_5$ and R$_6$ are each H.

29. The composition according to claim 23 wherein R$_5$ is F, Cl, OCH$_3$ or OCF$_3$ when R$_3$, R$_4$ and R$_6$ are each H.

30. The composition according to claim 23 two of R$_3$, R$_4$, R$_5$ or R$_6$ are independently F or Cl.

31. The composition according to claim 30 wherein R$_4$ and R$_5$ are independently F or Cl.

32. The composition according to claim 30 wherein R$_5$ and R$_6$ are independently F or Cl.

33. The composition according to claim 31 wherein R$_4$ and R$_5$ are Cl.

34. The composition according to claim 32 wherein R$_5$ and R$_6$ are Cl.

35. The composition according to claim 23 wherein R$_5$ is OPO$_3$H$_2$ or its pharmaceutically acceptable salt.

36. The composition according to claim 23 wherein R$_2$ is NO$_2$ when R$_3$, R$_4$ and R$_6$ are each H.

37. The composition according to claim 23 wherein R$_4$ is NO$_2$ and R$_2$, R$_3$ and R$_6$ are each H.

38. The composition according to claim 23 wherein R$_4$ is OCO(Glu) and R$_2$, R$_3$, R$_5$ and R$_6$ are each H.

39. The composition according to claim 38 wherein Glu is in the form of a pharmaceutically acceptable salt.

40. The composition according to claim 23 wherein R$_4$ is NHCO(Glu) and R$_2$, R$_3$, R$_5$ and R$_6$ are each H.

41. The composition according to claim 40 for wherein Glu is in the form of a pharmaceutically acceptable salt.

42. The composition according to claim 23 wherein R$_4$ is NHR$_7$ and R$_2$, R$_3$, R$_5$ and R$_6$ are each H.

43. The composition according to claim 42 for wherein R$_7$ is α-glutamyl or a pharmaceutically acceptable salt thereof.

44. The composition according to claim 43 wherein R$_7$ is H, α-glutamyl or a pharmaceutically acceptable salt thereof or a polyglutamic acid polypeptide residue or a pharmaceutically acceptable salt thereof.

45. A method of treating a tumor in a patient in need of therapy comprising administering to said patient an effective amount of a compound or its pharmaceutically acceptable salt according to the structure:

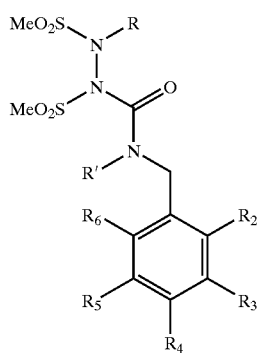

Where
R is —CH$_3$ or —CH$_2$CH$_2$Cl;

R' is C$_1$–C$_7$ alkyl or —CH$_2$CH$_2$Cl;

one of R$_2$ or R$_4$, but not both, is selected from OPO$_3$H$_2$, NO$_2$, OCO(Glu), NHCO(Glu) and NHR$_7$ and the other of R$_2$ or R$_4$ which is unassigned, and R$_3$, R$_5$ and R$_6$, are, independently selected from H, F, Cl, Br, I, OH, OPO$_3$H$_2$, OCH$_3$, CF$_3$, OCF$_3$, NO$_2$, CN, SO$_2$CH$_3$, SO$_2$CF$_3$, COCH$_3$, COOCH$_3$, SCH$_3$, SF$_5$, NHR$_9$, N(R$_9$)$_2$ and C$_1$–C$_7$ alkyl, with the proviso that at least two of R$_2$, R$_3$, R$_4$, R$_5$ and R$_6$ are H;

R$_7$ is H, glutamyl or a polyglutamic acid polypeptide residue —COCH(NHR$_{7a}$)CH$_2$CH$_2$CO$_2$H where R$_{7a}$ is glutamyl or a polyglutamic acid polypeptide residue having from 1 to 50 peptide linkages;

R$_8$ is H or C$_1$–C$_7$ alkyl; and

R$_9$ is CH$_3$ or CH$_2$CH$_3$;

optionally, in combination with a pharmaceutically acceptable additive, carrier, or excipient.

46. The method according to claim 45 wherein R is —CH$_2$CH$_2$Cl.

47. The method according to claim 45 wherein said R' is methyl, ethyl, n-propyl, isopropyl, n-butyl, isobutyl, t-butyl, n-pentyl, isopentyl, n-hexyl, isohexyl or substituted hexyl.

48. The method according to claim 47 wherein R' —CH$_3$.

49. The method according to claim 45 wherein R$_2$ is OPO$_3$H$_2$ or a pharmaceutically acceptable salt thereof.

50. The method according to claim 45 wherein R$_4$ is F, Cl or OCH$_3$ and R$_3$, R$_5$ and R$_6$ are each H.

51. The method according to claim 45 wherein R$_5$ is F, Cl, OCH$_3$ or OCF$_3$ and R$_3$, R$_4$ and R$_6$ are each H.

52. The method according to claim 45 wherein two of R$_3$, R$_4$, R$_5$ or R$_6$ are independently F or Cl.

53. The method according to claim 52 wherein R$_4$ and R$_5$ are independently F or Cl.

54. The method according to claim 52 wherein R$_5$ and R$_6$ are independently F or Cl.

55. The method according to claim 53 wherein R$_4$ and R$_5$ are Cl.

56. The method according to claim 54 wherein R$_5$ and R$_6$ are Cl.

57. The method according to claim 45 wherein R$_5$ is OPO$_3$H$_2$ or a pharmaceutically acceptable salt thereof.

58. The method according to claim 45 wherein R$_2$ is NO$_2$ and R$_3$, R$_4$ and R$_6$ are each H.

59. The method according to claim 45 wherein R$_4$ is NO$_2$ and R$_2$, R$_3$ and R$_6$ are each H.

60. The method according to claim 45 wherein R$_4$ is OCO(Glu) and R$_2$, R$_3$, R$_5$ and R$_6$ are each H.

61. The method according to claim 60 wherein Glu is in the form of a pharmaceutically acceptable salt.

62. The method according to claim 45 wherein R$_4$ is NHCO(Glu) and R$_2$, R$_3$, R$_5$ and R$_6$ are each H.

63. The method according to claim 62 wherein Glu is in the form of a pharmaceutically acceptable salt.

64. The method according to claim 45 wherein R$_4$ is NHR$_7$ and R$_2$, R$_3$, R$_5$ and R$_6$ are each H.

65. The method according to claim 64 wherein R$_7$ is a α-glutamyl or a pharmaceutically acceptable salt thereof.

66. The method according to claim 64 wherein R$_7$ is H, a α-glutamyl or a pharmaceutically acceptable salt thereof or a polyglutamic acid polypeptide residue or a pharmaceutically acceptable salt thereof.

67. The method according to claim 45 wherein said cancer is selected from the group consisting of stomach, colon, rectal, liver, pancreatic, lung, breast, cervix uteri, corpus uteri, ovary, prostate, testis, bladder, renal, brain/CNS, head and neck, throat, multiple myeloma, melanoma, Ewing's sarcoma, small cell lung cancer, choriocarcinoma, rhabdomyosarcoma, Wilms' Tumor, neuroblastoma, mouth/pharynx, oesophagus, larynx, kidney or lymphoma.

68. The method according to claim 67 wherein said lymphoma is Hodgkin's disease or non-Hodgkin's lymphoma.

69. A method of treating a drug-resistant a tumor in a patient in need thereof, said method comprising administering to said patient an effective amount of a compound according to any of claims 1–22.

70. A method of treating a tumor in a patient in need thereof said method comprising administering to said patient an effective amount of a compound according to any of claims 1–22 in combination with at least one additional anti-tumor agent.

71. A method of treating a tumor in a patient in need thereof said method comprising administering to said patient an effective amount of a compound according to any of claims 1–22 in combination with at least one additional anti-tumor agent selected from the group consisting of antimetabolites, Ara C, etoposide, doxorubicin, taxol, hydroxyurea, vincristine, cytoxan, mitomycin C, adriamycin, topotecan, campothecin, irinotecan, gemcitabine and cis-platin.

72. A pharmaceutical composition comprising an effective amount of a compound according to any of claims 1–22 in combination with at least one additional anti-tumor agent.

73. A pharmaceutical composition comprising an effective amount of a compound according to any of claims 1–22 in combination with at least one additional anti-tumor agent selected from the group consisting of antimetabolites, Ara C, etoposide, doxorubicin, taxol, hydroxyurea, vincristine, cytoxan, mitomycin C, adriamycin, topotecan, campothecin, irinotecan, gemcitabine, campothecin and cis-platin.

* * * * *